(12) United States Patent
Krause

(10) Patent No.: US 12,403,098 B2
(45) Date of Patent: Sep. 2, 2025

(54) PHARMACEUTICAL DOSAGE FORM FOR APPLICATION TO MUCOUS MEMBRANES AND METHODS FOR PRODUCING SAME

(71) Applicant: ESOCAP AG, Basel (CH)

(72) Inventor: Julius Krause, Greifswald (DE)

(73) Assignee: Esocap AG, Basel (CH)

( * ) Notice: Subject to any disclaimer, the term of this patent is extended or adjusted under 35 U.S.C. 154(b) by 876 days.

(21) Appl. No.: 17/439,385

(22) PCT Filed: Mar. 13, 2020

(86) PCT No.: PCT/EP2020/056934
§ 371 (c)(1),
(2) Date: Sep. 14, 2021

(87) PCT Pub. No.: WO2020/183005
PCT Pub. Date: Sep. 17, 2020

(65) Prior Publication Data
US 2022/0151939 A1    May 19, 2022

(30) Foreign Application Priority Data

Mar. 14, 2019 (EP) .................................... 19162908
Aug. 21, 2019 (EP) .................................... 19192961

(51) Int. Cl.
| | |
|---|---|
| *A61K 9/48* | (2006.01) |
| *A61J 3/07* | (2006.01) |
| *A61K 9/00* | (2006.01) |
| *A61K 9/70* | (2006.01) |
| *A61K 31/196* | (2006.01) |
| *A61K 47/10* | (2017.01) |
| *A61K 47/32* | (2006.01) |
| *A61K 47/38* | (2006.01) |

(52) U.S. Cl.
CPC ............ *A61K 9/4808* (2013.01); *A61K 9/006* (2013.01); *A61K 9/7007* (2013.01); *A61K 31/196* (2013.01); *A61K 47/10* (2013.01); *A61K 47/32* (2013.01); *A61K 47/38* (2013.01)

(58) Field of Classification Search
CPC .... A61K 9/4808; A61K 9/006; A61K 9/7007; A61K 47/38; A61J 3/074; A61M 31/002
See application file for complete search history.

(56) References Cited

U.S. PATENT DOCUMENTS

| | | |
|---|---|---|
| 5,167,962 A | 12/1992 | Lew et al. |
| 6,183,466 B1 | 2/2001 | Wong et al. |
| 7,037,275 B1 | 5/2006 | Marshall et al. |
| 2003/0044446 A1 | 3/2003 | Moro et al. |
| 2011/0174653 A1* | 7/2011 | Schwarz ........... A61M 15/0043 |
| | | 206/461 |
| 2012/0321706 A1 | 12/2012 | Masri et al. |
| 2014/0335153 A1 | 11/2014 | Allen et al. |
| 2018/0036251 A1* | 2/2018 | Bogdahn .............. A61K 9/7007 |

FOREIGN PATENT DOCUMENTS

| | | |
|---|---|---|
| CN | 107249575 A | 10/2017 |
| JP | H05097659 A | 4/1993 |
| JP | 2003508106 A | 3/2003 |
| JP | 2010159268 A | 7/2010 |
| JP | 2013129669 A | 7/2013 |
| JP | 2018501878 A | 1/2018 |
| RU | 2094044 C1 | 10/1997 |
| WO | WO-2005039499 A2 | 5/2005 |
| WO | WO-2010135053 A2 | 11/2010 |
| WO | WO-2013003487 A1 | 1/2012 |
| WO | WO-2015059569 A1 | 4/2015 |
| WO | WO-2016102067 A1 | 6/2016 |

* cited by examiner

*Primary Examiner* — Mina Haghighatian
(74) *Attorney, Agent, or Firm* — Dorsey & Whitney LLP

(57) ABSTRACT

The present invention relates to a pharmaceutical dosage form for application to a mucous membrane, in particular to a buccal, intestinal, rectal or vaginal mucous membrane, comprising at least one string-like or strip-like preparation comprising the active pharmaceutical ingredient, the dosage from being configured to be wettable during a step of administration to a patient. The invention also relates to a method of producing the pharmaceutical dosage form.

20 Claims, 9 Drawing Sheets

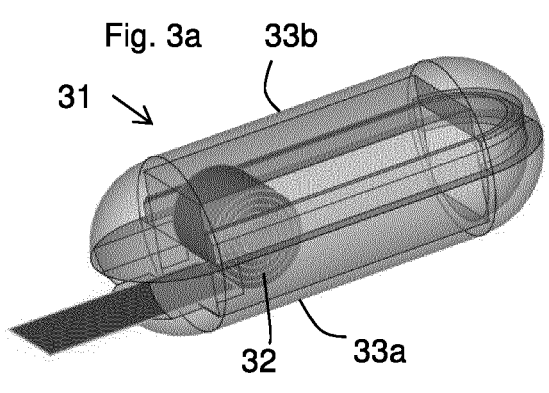
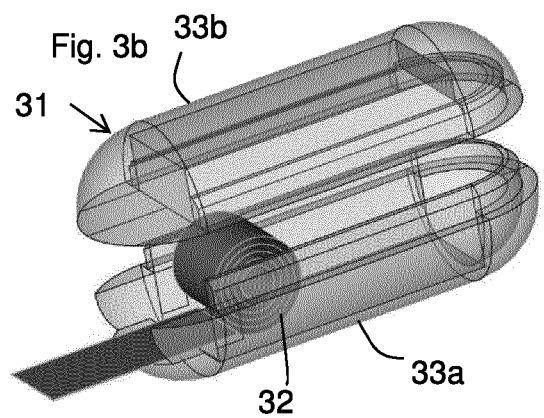
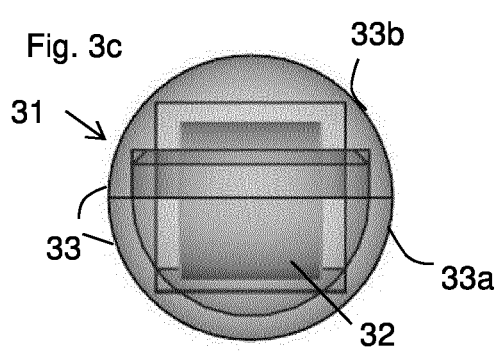
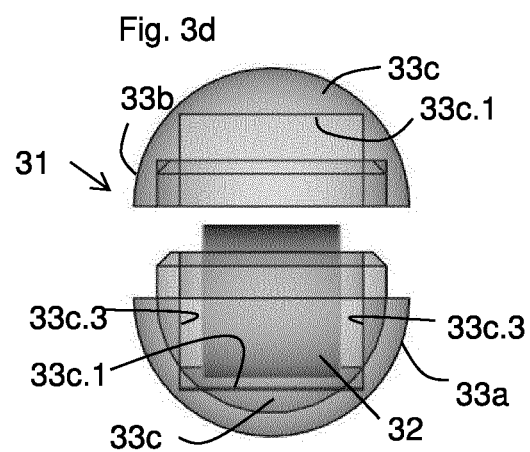
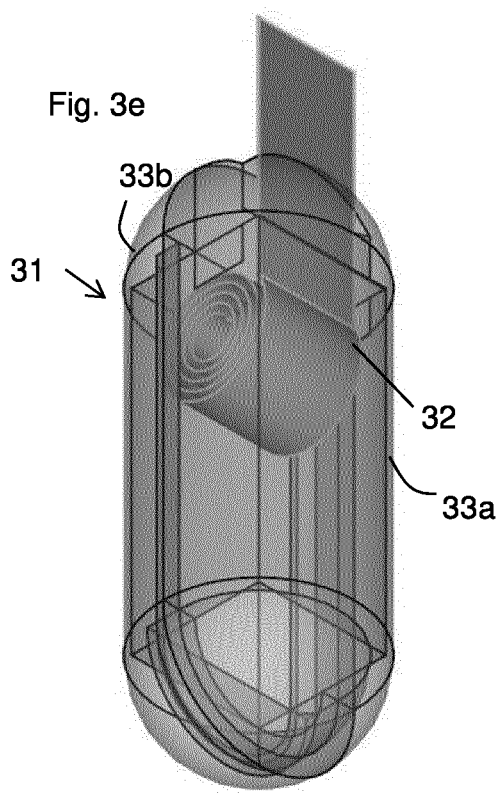
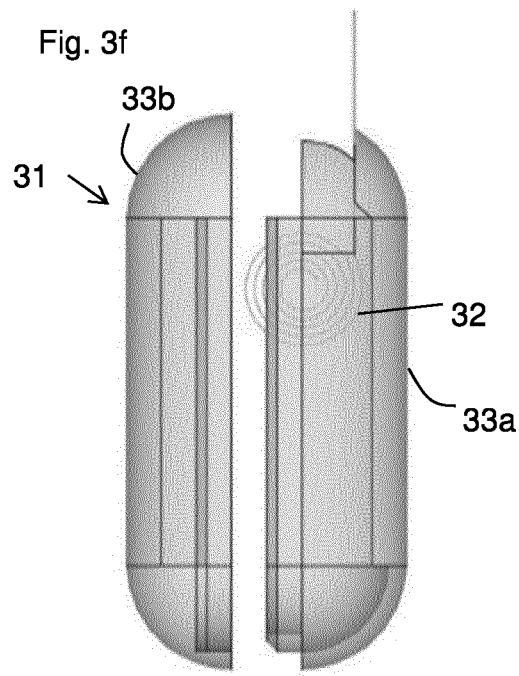

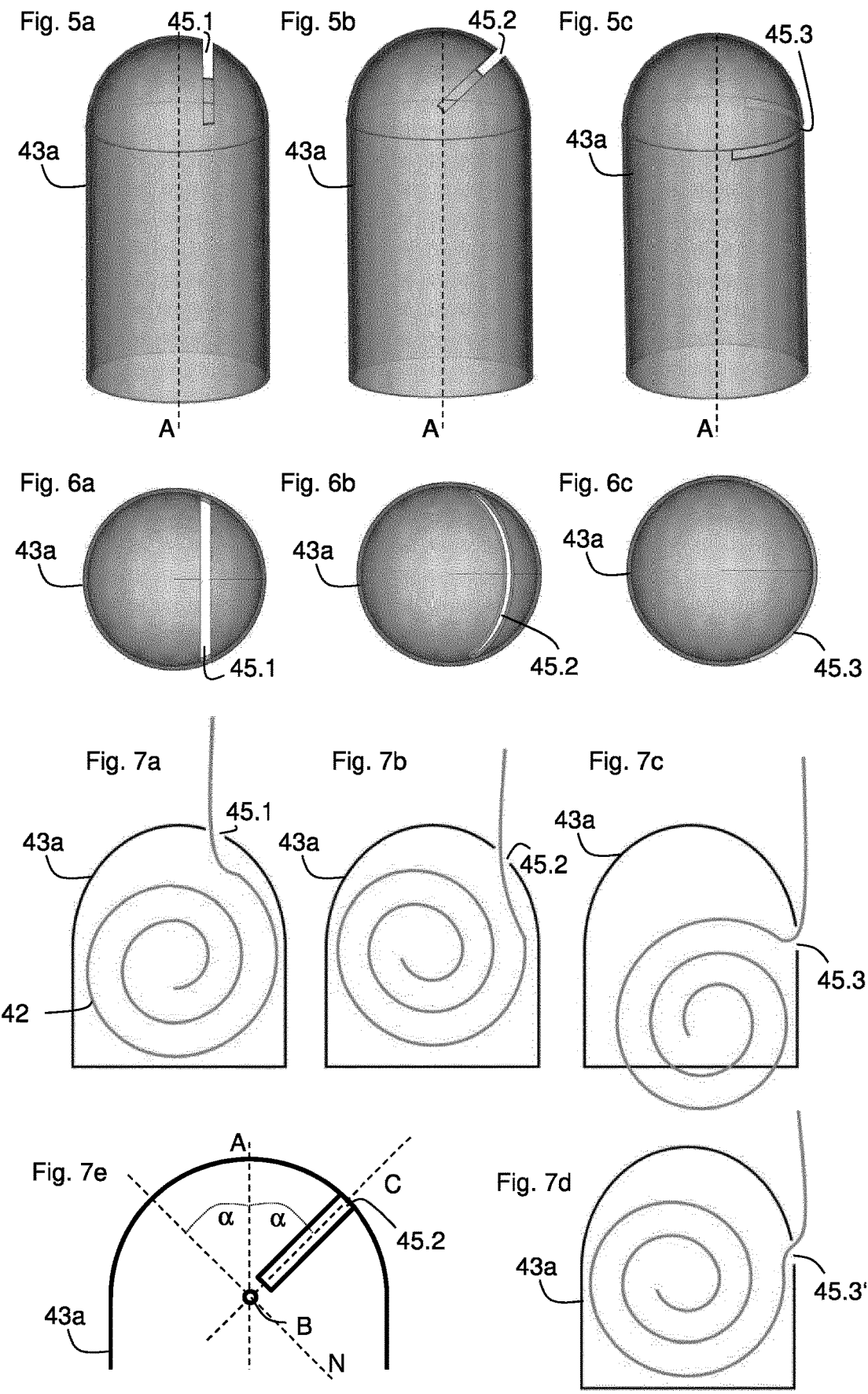

Testing and Selection Protocol 1

Development Film Formulation

Optical assessment:
- homogeneous appearance
- no inclusions of air bubbles  ————————→ discard
- smooth surface                                    no ↓ yes

- Can the wafer be detached from the release liner well  ————————→ discard
- Can the wafer be cut well                                                              no ↓ yes Measurement
- layer thickness
- weight/cm$^2$

↓

Disintegration time                         ————————→ discard
- in 10 mL of water                          more than 120 sec
- on alginate film (simulation of a mucous membrane)

↓ less than 120 sec

Elasticity/Flexibility
- tensile strength (less than 0.005 Mpa)
- elongation until breaking = stretchiness (more than 40%)  ————————→ discard
- folding durability (more than 100)                                                      no ↓ yes suitable for further development

FIG. 11

PHARMACEUTICAL DOSAGE FORM FOR APPLICATION TO MUCOUS MEMBRANES AND METHODS FOR PRODUCING SAME

CROSS-REFERENCE TO RELATED APPLICATIONS

The present application is a continuation under 35 U.S.C. § 371 of International Application No. PCT/EP2020/056934 which claims priority to European Patent Applications Nos. EP19162908.8, filed on Mar. 14, 2019, and EP19192961.1, filed on Aug. 21, 2019, the contents of both are incorporated herein by reference in their entirety.

The present invention relates to a pharmaceutical dosage form for application on a mucous membrane, in particular buccal, gastro-intestinal, rectal or vaginal mucosa. The invention also relates to a method of producing the pharmaceutical dosage form and a method of producing a capsule device for a pharmaceutical dosage form.

Such dosage forms are known from WO 2016/102067 A1. The pharmaceutical dosage form of WO 2016/102067 A1 is designed such that it comprises at least one sheet like, in particular film shaped, foil shaped or wafer shaped preparation comprising the active pharmaceutical ingredient, a release mechanism, and a trigger mechanism, wherein the trigger mechanism is adapted to trigger, at a predetermined site of action, in particular of the gastrointestinal tract, of the rectum or of the vagina, the release of the sheet like preparation by the release mechanism.

From the embodiment according to FIGS. 8a, 8b, 8c of WO 2016/102067 A1, a dosage form is known having an elongated, strip-shaped preparation, which comprises the active pharmaceutical ingredient, the preparation being capable to be arranged in a compact condition and in an expanded condition, the dosage form having a capsule comprising a hollow space for accommodating the compacted preparation, the capsule device having an aperture and a first end of the preparation extending, in the compact condition, through the aperture for allowing pulling out the preparation from the hollow space into the surrounding area of the capsule thereby transferring the preparation from the compact condition to the expanded condition.

In experiments of the inventors it was surprisingly found that a wetting of the compacted sheet-like preparation during administration of the dosage form to the desired site of action is not a situation to be generally avoided but is rather beneficial for improving the reliability of the mechanical process of expanding the preparation from the compacted condition to the expanded condition. Pull out tests showed that the maximum pulling force for pulling out the preparation from the capsule is generally lower under wet conditions compared to dry conditions. In consequence, the dosage form can be easily administered to the site of action and the risk of rupturing the sheet like preparation decreases.

Based on the experimental findings, the problem underlying the present invention is to improve the reliability of the mechanical process of expanding the preparation from the compacted condition to the expanded condition.

The problem is solved by the pharmaceutical dosage form of claim 1, the method of producing a capsule device for a pharmaceutical dosage form according to claim 15 and the method of producing a pharmaceutical dosage form according to claim 16. Preferred embodiments of the invention are subject matter of the dependent claims.

According to the invention, the opening and the preparation are dimensioned such that, when the preparation is pulled out from the opening, a spacing is provided in the opening cross section of the opening between the preparation and a surface of the capsule device defining the opening. Due to the spacing in the opening, any friction between the preparation and the capsule surface defining the opening is minimized and the risk of a jamming of the elongated preparation is reduced, when the preparation is pulled out through the opening. Moreover, a wetting of the preparation inside the capsule device is possible, for example by rinsing the opening of the capsule device with water. The wetting may be achieved, for example, during an oral administration of the dosage form, where the patient swallows the dosage form with a mouthfull of water. The resulting advantage of the configuration of the dosage form according to the invention is that the reliability of the mechanical process of expanding the preparation from the compacted condition to the expanded condition is enhanced.

The shape of the opening preferably corresponds to the outer contours of the elongated preparation in the plane perpendicular to the length axis of the elongated preparation. For example, a slit-like opening is preferred in case of a strip-like preparation, and a circular opening may be provided in case of a string-like preparation. Here the opening basically provides a rectangular passage cross-section, and the cross section of the strip-like preparation is also basically rectangular. In case of a string-like preparation, the opening may provide a circular passage cross-section, and the cross section of the strip-like preparation may also be basically circular. This way, the motion of the elongated preparation with respect to the capsule device is guided by the opening and the relative position of the capsule device and the preparation is stabilized while pulling out the preparation from the capsule device.

Preferably, the opening is a slit-like opening configured for allowing a strip-like preparation to pass through the opening, wherein preferably, the cross section (CS) of the opening being larger than the cross section of the strip-like preparation, when the latter is moving through the opening. Herein, the cross-section of the opening defines a surface, and the cross-section of the strip-like preparation is preferably measured within said surface, the strip-like preparation preferably being centered within the opening.

The spacing S in the opening cross section of the opening between the elongated preparation and a surface of the capsule device defining the opening is preferabyl measured when the cross section of the opening and the cross section of the elongated preparation are centered with a virtual axis A running lenghtwise through the capsule device. The dimension of the opening resulting in a spacing S is preferably calculated by a dimension a, being a diameter or a width of the opening, t being a diameter of a string-like preparation or a thickness of a strip of a strip-like preparation, wherein a=t+2*S, cf. FIG. 1c.: S is preferably ranging from 10 to 2000, or 20 to 1500, or 50 to 1000, or 100 to 750, or 200 to 500 or 300 to 400 micrometer (μm), respectively. S is larger than Null and is preferably larger than the value t, in particular S=f*t, f being a numerical factor chosen from 1 to 20, preferably from 2 to 15, more preferably from 3 to 12. The dimension a is preferably chosen such that it ranging from 100 to 4000, 100 to 2000, or 200 to 1500 or 300 to 1000, or 400 to 800 or 500 to 700, or 600 micrometer (μm), respectively.

In case of a strip-like preparation and a slit-like opening, the length c of the passage cross section, through which the strip-like preparation passes when being pulled outwards, is larger than the width w of the strip of the strip-like preparation. The passage cross section is larger than the cross-section of the elongated preparation in the same plane.

The capsule device is generally a container being configured for a buccal, gastro-intestinal, rectal or vaginal administration, respectively. In particular, the capsule device is a swallowable object, which means, in particular, that the dimensions and the outer shape of the capsule device are suitable for swallowing the capsule device.

The capsule device may be a capsule, including a hollow-cylinder, which is capped on both sides by curved cap members. A cap member may have basically the shape of a semi-sphere. A cap-member may be manufactured with a cylindrical portion as one piece. Two parts of a capsule device may be joined to form the capsule device—this facilitates assembling the dosage form by first placing the preparation inside one of the two parts, and then securing the preparation by joining the two parts of the capsule device. A capsule may also be shaped to have an elliptical or oval cross section, such that the capsule has the shape of an olive, for example.

The capsule device may have an elongated shape, which means that a length measured along a virtual central axis A of the capsule device is larger than its lateral outer dimension(s). The capsule device, without considering the opening, may be rotationally symmetric with respect to the central axis A.

The capsule device may have more than one opening, in particular two openings, or more than two openings.

In a preferred embodiment, the capsule device is configured such that the opening is offset from the central axis A, which means that the central axis A does not cross the opening cross section or which means that the central axis A does not cross a central point of the opening cross section. An advantage of such an embodiment is that the force acting on the wall, which forms the capsule device, when the preparation is pulled out from the capsule device and the capsule device is administered to a patient, is reduced and the risk of damaging the capsule device is thereby reduced. In experiments of the inventors it was found that, in particular for a strip-like preparation, the unwinding of a rolled preparation through an opening—being arranged offset from the central axis A—is facilitated compared to a central position of the opening, the central position being such that the central axis A of the capsule device runs through a center of the opening.

In case of a slit-like opening, the opening is preferably arranged offset from the central axis A of a capsule device. The slit is formed by opposing surfaces of the wall, which forms the capsule device.

For example, the preferred shape of a slit is achieved when milling off the wall, which forms the capsule device, such that a plate-shaped volume is subtracted from the capsule wall —when considering the capsule device and the cut volume to be three-dimensional mathematical objects. The orientation of the plate-shaped volume subtracted from the capsule material is characterized by the orientation of the main plane of the plate-shaped volume, in particular with respect to the direction of the virtual central axis A of the capsule device. In FIG. 7e, the main plane is defined by the lines C and B, B being perpendicular to the drawing surface and perpendicular to A. The resulting shape of a slit is referred to as "planar curved slit" hereinafter, wherein the slit follows the outer curved contour of a capsule device but is straight when viewed perpendicular to the opening cross section or respectively, when viewed in the main plane. The length b of the slit (cf. FIG. 1b) runs in parallel to the main plane B-C (see FIG. 7e). This may be achieved by using a planar milling tool, e.g. a planar saw blade, or by another tool resulting in a plate-shaped cutting volume, e.g. a cylindrical milling head performing a lateral motion or by using a laterally moved waterjet in process of abrasive waterjet cutting. Furthermore, the slit may be generated using a laser to cut or to ablate material from the capsule material. Moreover, punching may be used to generate the slit through the capsule material to create a slit-shaped hole via shearing. However, the opening may also be created by injection molding of a suitable material, e.g. plastic, forming the capsule device. The opening preferably has the shape of a planar curved slit. The planar property of the curved slit offers the advantage that the passage of a strip-like preparation through the slit in a pull-out direction P is facilitated, and thereby, the reliability of the mechanical process of expanding the preparation from the compacted condition to the expanded condition is further improved.

The slit-like opening is preferably arranged such that the normal N of the main plane of the planar curved slit and the central axis A of the capsule device include an angle $\alpha$, wherein preferably $0° < \alpha < 90°$ (cf. FIG. 7e). In a preferred configuration of the slit-like opening, where the slit-like opening is offset from the central axis A of the capsule device, the angle $\alpha$ is Null. In another preferred configuration of the slit-like opening, the angle $\alpha$ is 45°, and in a more preferred embodiment, the angle $\alpha$ is 90°.

The slit-like opening is preferably arranged such that a main plane running through the opening is in parallel to an axis B, which is perpendicular to the central axis A of the capsule device (cf. FIG. 7e). Such a configuration matches to a winding of a strip-like preparation, which is wound around a winding axis being parallel to axis B, and facilitates the unwinding process.

Preferably, the capsule device comprises a guiding member, which is arranged inside the inner space of the capsule device to guide the motion of the string-like or sheet like preparation towards the opening of the capsule device. The guiding member may be a part of the inner wall of the capsule device or a part, in particular a wall member, being supported by the inner wall of the capsule device or being connected to the inner wall of the capsule device.

The capsule device may contain an auxiliary device being configured to guide a coiling and/or uncoiling of a string-like preparation or a winding and/or unwinding of a strip-like preparation, in particular by coiling or winding the preparation around one or more rods or cylinders of the auxiliary device. The rod or cylinder may be rotatably disposed inside the capsule device for facilitating uncoiling or unwinding.

The hollow space inside the capsule device is defined by at least one inner wall of the capsule device. In a preferred embodiment, the capsule device is defined by one wall, which has an outer side, facing the surrounding of the capsule device and having an inner side facing the hollow space. Preferably, the inner side (inner surface) and the outer side (outer surface) run in parallel to each other, which means that the outer contour surface of the hollow space is similar to the outer contour surface of the capsule device. However, it is also possible and preferred that the inner surface of the capsule device is at least portion-wise not in parallel to the outer contour surface of the capsule device. Such a configuration allows defining auxiliary structures inside the capsule device, which assist in guiding the motion of the preparation inside the capsule device or other function. Preferably, the auxiliary structure is an inner guiding wall of the capsule device, which is arranged for guiding the uncoiling and/or unwinding of the preparation inside the capsule device. The guiding wall is arranged for guiding the positioning of the preparation during uncoiling and/or unwinding of the preparation. Preferably, the guiding wall is arranged in parallel to the direction P of the movement, by which the preparation is moved inside the capsule device towards the opening. Preferably, the guiding wall is arranged to be aligned with the opening.

Preferably one or more inner walls of the capsule device are arranged to form a guiding compartment inside the capsule device. The guiding compartment is arranged to support the preparation in its compact condition and assists in unwinding the preparation. Preferably, the one or more inner walls of the capsule device are arranged to form side walls of a cuboid hollow space, which accommodates the preparation in its compact condition.

In another preferred embodiment, the pharmaceutical dosage form, in particular the capsule device, comprises a sinker device. The sinker device is configured to provide negative buoyancy to the capsule device. In experiments of the inventors underlying the finding of this preferred embodiment it was found that reducing the buoyancy, for example by increasing the mass of the capsule device, leads to an improved reliability of the mechanical process of expanding the preparation from the compacted condition to the expanded condition. In case of strip-like preparation, the unwinding of the preparation from the compacted condition, where the strip-like preparation is wound around a winding axis, to the expanded condition was significantly facilitated and more efficient. The problem underlying the preferred embodiment is the observation that the transfer of the preparation from the compacted condition to the expanded condition is sometimes incomplete. While the invention already improves the efficiency of expansion, or respectively, unwinding, by providing a spacing between the opening and the preparation, the sinker device additionally increases the efficiency of expansion. It is assumed that the capsule device, also if properly swallowed by a patient in the presence of water or aqueous solution, is not completely filled with water but air-bubbles sometimes remain inside the capsule device. The air contributes to buoyancy, and the sinker device assists to resist the buoyancy effects by assisting in the displacement of air or by using denser materials than water for utilizing gravity.

The sinker device may be realized by various preferred configurations. The sinker device may be configured to comprise at least one sinker element, preferably exactly one sinker element, the sinker element being an insert part or an attachment part, respectively preferably having a density higher than air, which is about 1.2 kg/m$^3$.

A sinker element being an insert part is preferably inserted, preferably loosely inserted, or preferably attached, inside the hollow space of the capsule device. An insert part occupies a specific occupied volume inside the hollow space of the capsule device. The occupied volume, in consequence, cannot be occupied by air any more. Thereby buoyancy is reduced. In case that the density of the insert part is higher than the density of water, which is about 1 g/cm$^3$, the expansion of the compacted preparation is also supported by the surplus weight of the insert part—the surplus weight being the weight of the difference between the mass of the insert part and the mass of the water displaced by the insert part. The insert part may be attached to an inner wall of the capsule device, for example by a force-fit connection or by an adhesive, which is preferably soluble in water. Preferably, the insert part is attached to the inner sides of the capsule device by dimensioning the insert part such that the insert part is clamped inside the capsule device between sections of the inner wall of the capsule device, e.g. between opposing sections of the inner wall. For example, an insert part having a circular cross section of radius R may be inserted into a capsule device having substantially the same or a slightly smaller circular cross section with radius R.

The sinker element may be attached to any part of the pharmaceutical dosage form, thereby forming an attachment part of the pharmaceutical dosage form, or the capsule device, respectively. The attachment part may in particular be attached to the outer surface of the pharmaceutical dosage form, or to the capsule device, respectively. The density of the attachment part or a portion of the same is preferably higher than the density of water, which is about 1 g/cm$^3$.

The density of the sinker element or a material comprised by the sinker element is preferably higher than 1.2 kg/m$^3$, preferably higher than the density of water measured at 21° C., and is preferably higher than 1.0 g/cm$^3$. The density of the sinker element or a material comprised by the sinker element is preferably between 1.0 g/cm$^3$ and 2.0 g/cm$^3$. This range is achieved by many water-soluble materials like sucrose, dextrose, lactose, fructose, each material being preferred. Preferred materials are also microcrystaline cellulose, sorbitol, xylitol, isomalt and gelatin. It is also preferred that the density of the sinker element or a material comprised by the sinker element is preferably between 1.0 g/cm$^3$ and 20.0 g/cm$^3$, 1.0 g/cm$^3$ and 5.0 g/cm$^3$, 1.0 g/cm$^3$ and 10.0 g/cm$^3$, thereby including even much denser material, for example metal, preferably tungsten. Such sinker elements are also referred to as "weight element".

In a preferred embodiment, the sinker element comprises or consists of pressed material, in particular a granular substance or mixture, the material comprising or consisting of a dicalcium phosphate, preferably anhdyrous dicalcium phosphate, preferably in a concentration of preferably 93 mol % to 99 mol %, preferably 98 mol %. The material may also comprise croscarmellose sodium, preferably in a concentration of preferably 0.25 mol % to 0.75 mol %, preferably 0.5 mol %, which particularly acts as a disintegrant. The material may also comprise magnesium stearate, preferably in a concentration of preferably 1.0 mol % to 2.0 mol %, preferably 1.5 mol %, which particularly acts as a glidant and/or a lubricant. The material may also comprise colloidal silicon dioxide, preferably in a concentration of preferably 0.25 mol % to 0.75 mol %, preferably 0.5 mol %, which particularly acts as a flow-regulating agent and/or disintegrant. A material composed of one or more of said components or analogous components is preferably substantially water-insoluble, the material desintegrates by way of a disintegrant component. The material may comprise further suitable excipients. calcium hydrogene phosphate dihydrate, preferably in a concentration of 93 to 98 mol % (93-98% m/m), preferably acting as a filler material. Disintegrants: soy polysaccharide 0.25-5%; polyvinylpyrrolidone 0.25-5%; sodium starch 0.25-5%. Lubricants and form release agents: magnesium stearate 0.25-2.5%. Glidants: highly disperse silica 0.25-1.5%. Further possible auxiliary excipients: fillers: starch (corn-, potatoe, pea-, wheat-); lactose; barium sulfate; sodium chloride; urea; PEG. Lubricants: talc; calcium behenate; glycerol monostearate; stearic acid; hydrogenated vegetable fats; PEG 4000.

The invention is also related to a method of producing a sinker element by tablet pressing a granular material, in particular a powder mixture, which material is defined in the previous paragraph, into a shape, in particular a substantially cylindrical shape, the shape preferably fitting inside the hollow space of the capsule device, in particular in a half part of the capsule device. The invention is also related to a method of producing a pharmaceutical dosage form, which method comprises the step of producing a sinker element, in particular by providing a granular material, in particular a powder mixture, which material is proposed in the previous paragraph, and by tablet pressing said material into a shape, in particular a substantially cylindrical shape, the shape preferably fitting inside the hollow space of the capsule device, in particular in a half part of the capsule device. Tablet pressing may utilize any eccentric press, or a rotary press. Alternatively, the method of producing the sinker element may also utilize casting, injection molding or 3D printing a sinker element.

The sinker device, a sinker element of the sinker device or a weight element, respectively, preferably, consists of or comprises a material, which is water-soluble. It is also possible and preferred that the sinker device or the weight element, respectively, consists of or comprises a material, which is not water-soluble.

The sinker device may also comprise a sinker element, respectively an insert part, which is configured to be filled with water, once the pharmaceutical dosage form is administered to a patient in the presence of water or aqueous solution. For this purpose, the insert part preferably comprises at least one opening or channel. Preferably the insert part or a part of the same is porous by comprising an open pored material, thereby allowing water to enter the inner volume of the pores and allowing the water displacing the air. A suitable porous material may be a fibrous material or granular material, or mesh-like material, woven material or non-woven material. The porous material may be a cellulose material. The porous material may be a paper material or textile material.

The sinker device may also comprise at least one pore in the wall of the capsule device, which allows water to enter the hollow space and allows air to leave the hollow space. The wall of the capsule device may, in addition to the opening for the preparation, contain at least one pore in the wall of the capsule device, which allows water to enter the hollow space and allows air to leave the hollow space. Such at least one pore may be provided in a curved—in particular half-sphere-shaped—face wall of the capsule, or in both opposing curved face walls, and/or in other sections of the capsule, e.g. in the hollow-cylindrical wall sections of the capsule. It is possible and preferred that the wall of the capsule device only contains the opening (5) serving as a passage for the preparation, and, in particular, does not contain any other pore or opening.

It is preferred that the sinker element is arranged, preferably attached, to a half of the capsule device, and being, in particular, not arranged in the other half of the capsule device. Thereby, a sufficient portion of the hollow space, in particular inside said other half, inside the capsule is available for the preparation in its compacted form. In case that the sinker element is attached, e.g. clamped or adhered to the capsule device, it is guaranteed that the expansion of the preparation from its compacted form to its expanded form, e.g. by unwinding, is not hindered by the sinker element.

The sinker element may be an insert part, which fits inside the hollow space of the capsule device. The shape of the insert part may be cylindrical.

The sinker device may also be implemented such that the walls of the capsule device have a dense material, preferably having a density >1.0 g/cm$^3$, the capsule wall thereby acting as a sinker element or weight element, respectively. The sinker device may also be implemented such that a sinker element is attached outside the capsule device, e.g. using a weight element connected to an outer wall, preferably a curved face wall, of the capsule device, the connection preferably being an adhesion connection, and/or using a deformable connector, e.g. a filament, for allowing the sinker element being arranged in a distance to the capsule wall.

Especially, the present invention relates to a pharmaceutical dosage form for the application, preferably to an upper gastrointestinal tract such as throat, esophagus, cardia and/or stomach, and particularly to the respective mucous membranes, that enables a local drug therapy and/or diagnostic investigation. Local diseases, in particular diseases of the esophagus, can be treated with local acting drugs. However, generally current pharmaceutical dosage forms or application systems often do not target the specific diseased location; particularly they do not target the esophagus and/or its mucous membrane. Therefore, generally a large amount of the applied drug, particularly the active pharmaceutical ingredient, is absorbed systemically, which may cause side effects, in particular adverse reactions. In particular, it is therefore an object of the present invention to improve the local application of a drug, particularly an active pharmaceutical ingredient. Preferably, certain embodiments according to the present invention specifically achieve and/or only aim for this object of the present invention. Moreover, certain embodiments according to the present invention may achieve further objects of the present invention. Furthermore, certain embodiments of the present invention may have the object to increase the bioavailability of an active pharmaceutical ingredient, locally deliver a useful substance, preferably a drug such as an active pharmaceutical ingredient, treat the esophagus with a local acting drug and/or reduce side effects, in particular adverse reactions.

In particular, the present inventors make use in an advantageous manner of the different permeability of various mucous membranes and particularly their suitability for taking up various drugs, which are inter alia different in their molecular size and lipophilicity, to provide a dosage form which allows a direct contact of the dosage form with the mucous membrane after the release at a predetermined site of action.

In particular, the present invention is a pharmaceutical dosage form for the application to mucous membrane, in particular to a buccal, intestinal, rectal or vaginal mucous membrane.

Such a pharmaceutical dosage form according to the present invention advantageously allows improving the bioavailability of active pharmaceutical ingredients which are, in particular, contained in orally, vaginally, or rectally administered drugs, at a predetermined site of action. In addition, a release of the active pharmaceutical ingredient at its predetermined site of action is achieved by the pharmaceutical dosage form according to the present invention, whereby, in particular, the amount of the active pharmaceutical ingredient available for resorption can be increased as well as an increased bioavailability and an increased resorption rate can be achieved.

In particular, this is achieved with the dosage form according to the present invention by the fact that a dosage form according to the present invention rapidly releases a string-like or strip-like, in particular a sheet-like, film-shaped, foil-shaped, or wafer-shaped, preparation comprising the active pharmaceutical ingredient at a predetermined site of action with a systemic effect. Furthermore, the dosage form according to the present invention makes it possible to apply active pharmaceutical ingredients, which cannot be administered orally due to poor bioavailability, at a predetermined site of action.

Preferably the predetermined site of action is a mucous membrane, in particular a buccal, gastro-intestinal, rectal or vaginal mucous membrane.

The pharmaceutical dosage form according to the invention thus allows advantageously a coming into contact, in particular a direct contact, with the predetermined site of action, in particular a mucous membrane, preferably a tissue absorbing the active pharmaceutical ingredient, and further advantageously an uptake of the drug into the blood. The embodiment of the preparation comprising the active pharmaceutical ingredient is a string-like or strip-like, in particular sheet-like, film-shaped, foil-shaped, or wafer-shaped preparation, in particular a so-called wafer, advantageously allows a release of the sheet-like preparation directly onto a mucous membrane and a coming into contact, preferably coming into contact with a relatively large surface area, at the predetermined site of release, respectively site of action, whereupon the sheet-like preparation can dissolve and release the active pharmaceutical ingredient. Such a coming into contact with the predetermined site of action advantageously allows an enhanced resorption of the active pharmaceutical ingredient, in particular a resorption of the active pharmaceutical ingredient to the mucous membrane, and the amount of the active pharmaceutical ingredient available for resorption is thereby increased. An increased bioavailability and/or an increased rate of absorption are thereby achieved, too.

Advantageously, an intestinal first-pass effect, i.e. a conversation of the active pharmaceutical ingredient during its first passage through the intestinal mucosa and possibly also through the liver, in particular of an orally administered dosage form, can be reduced by a pharmaceutical dosage form according to the invention. Also, the destruction of the active pharmaceutical ingredient before it reaches a predetermined site of action, e.g. by gastric acid and/or digestive enzymes, can be advantageously reduced by a pharmaceutical dosage form according to the invention. The bioavailability of the active pharmaceutical ingredient is also advantageously increased by a pharmaceutical dosage form according to the invention. A pharmaceutical dosage form according to the invention particular advantageously allows a reduction in dose maintaining approximately an equal therapeutic effect, especially when compared to an application of a comparable conventional preparation, such as tablets, solutions, vaginal creams or suppositories. Furthermore, a pharmaceutical dosage form according to the invention advantageously allows a more accurate dosing of the active pharmaceutical ingredient as well as, where necessary, a reduction of side effects, especially gastrointestinal side effects. The pharmaceutical dosage form according to the invention further advantageously allows a relatively simple and discrete handling as well as a simple, particularly space-saving storage, wherein active pharmaceutical ingredients, which are comprised in the pharmaceutical dosage form according to the invention, may have an improved stability, e.g. at high heat and humidity, in particular compared to solutions and gels.

The pharmaceutical dosage form according to the present invention thus allows a targeted and complete adhesion to the predetermined site of action, respectively application site.

Further, this advantageously allows, inter alia, a prolongation of the residence time at the absorption window, a displacement of fluids which could lead to an early detachment or dissolution of the preparation, particularly of the wafer.

In a preferred embodiment of the pharmaceutical dosage form according to the present invention the pharmaceutical dosage form further comprises a shell, in particular a capsule, wherein the shell contains the at least one string-like or strip-like, in particular sheet-like, film-shaped, foil-shaped, or wafer-shaped preparation comprising the active pharmaceutical ingredient, and wherein preferably the shell comprises at least one opening through which a fluid surrounding the shell can come into contact with the inner space of the shell while the strip-like or string-like preparation is pulled out from the capsule device. Preferably the opening is formed as a slit and/or the opening is formed having a circular or oval cross section. A slit may have rounded corners and may be formed by a single surface Sa.

In particular, the capsule device of the dosage form makes it possible to protect the preparation by the construction capsule device against an unwanted release.

It is to be understood that a pharmaceutical dosage form according to the invention may comprise a capsule device which contains at least one or more sheet-like preparations comprising the active pharmaceutical ingredient.

The release of the sheet-like preparation by the release mechanism preferably takes place by at least partially moving out the preparation from at least a part of the capsule device.

The opening of the capsule device allows in a particular advantageous manner an entry and/or a coming into contact of the fluid surrounding the shell, when the preparation is pulled out from the capsule device, which means while the dosage form is administered to the respective site of action. The wetting of the preparation inside the capsule device facilitates pulling out the preparation from the capsule device during (or shortly before) the administration and thereby facilitates the administration and the reliability of the pulling-out process is improved.

In a preferred embodiment of the pharmaceutical dosage form according to the present invention the opening is formed as a slit. Such a slit may be embodied in different arrangements and configurations. For example, such a slit may be completely or partially circumferentially arranged at the capsule device. A slit that is completely circumferentially arranged at the capsule device may be arranged such that the slit divides the shell into multiple, in particular two parts, which may be connected by connector portions of the capsule device. In a preferred embodiment of the pharmaceutical dosage form according to the present invention the capsule device is formed out of a material that is essentially insoluble in a fluid which is present at the predetermined site of administration, in particular of the gastrointestinal tract. However, it is to be understood that such a capsule device may not just be insoluble at the site of administration but also at other compartments that have to be passed to reach the site of administration—in other words, on the complete path thereto.

In a preferred embodiment according to the present invention the capsule device consists of or mainly consists of a material that is essentially insoluble in a fluid which is present at the path of transporting the same to the site of administration, in particular of the rectum, of the vagina or of the gastrointestinal tract, preferably vaginal fluid respectively gastric juice.

A material that is essentially insoluble in vaginal fluid respectively gastric juice is preferably selected from the group comprising gastric juice-resistant polymers, comprising acidic polymethacrylates such as methacrylic acid:methyl methacrylate copolymers 1:1 (Eudragit L), methacrylic acid:methyl methacrylate copolymers 1:2 (Eudragit L), methacrylic acid:ethyl acrylate copolymer 1:1 (Eudragit L100-55), acidic cellulose derivatives such as hydroxypropyl methylcellulose acetate succinates (HPMCAS) -LF, -MF and/or -HF, HPMC acetate phthalate and cellulose acetate phthalate; acidic polymers based on vinyl alcohol such as polyvinyl acetate and vinyl acetate: crotonic acid copolymer; zein, keratin, gluten, shellac, gelatin and alginic acid hardened with formaldehyde or glutaraldehyde.

In a preferred embodiment of the pharmaceutical dosage form according to the present invention the capsule device is made out of a material that is selected from the group comprising hard gelatin, polymers, thermoplastics as e.g. Eudragit or the like. In this regard, in particular, materials can be beneficial that have been successfully tested, used and/or authorized already, e.g. for oral dosage forms.

In a further preferred embodiment of the pharmaceutical dosage form according to the present invention the capsule device consists of a material that is selected from the group consisting of hard gelatin or polymers.

In a preferred embodiment of the pharmaceutical dosage form according to the present invention the capsule device is formed as a capsule, wherein the shape of the capsule device may be generally chosen to allow the desired administration to a patient.

In a preferred embodiment of the pharmaceutical dosage form according to the present invention the capsule device is made of a material which is substantially insoluble in a fluid that is present on the path towards the site of administration, in particular inside the gastrointestinal tract, preferably insoluble in gastric juice, wherein preferably the shell consists of a material which is selected from the group comprising polymers and/or hard gelatin.

Preferably, such an essentially insoluble material, in particular essentially insoluble in vaginal fluid respectively gastric juice, is selected from the group comprising gastric juice-resistant polymers, comprising acidic polymethacrylates such as methacrylic acid:methyl methacrylate copolymers 1:1 (Eudragit L), methacrylic acid:methyl methacrylate copolymers 1:2 (Eudragit L), methacrylic acid:ethyl acrylate copolymer 1:1 (Eudragit L100-55), ammonio methacrylate copolymers (e.g Eudragit RS), acidic cellulose derivatives such as hydroxypropyl methylcellulose acetate succinates (HPMCAS) -LF, -MF and/or -HF, HPMC acetate phthalate and cellulose acetate phthalate; acidic polymers based on vinyl alcohol such as polyvinyl acetate and vinyl acetate: Crotonic acid copolymer; zein, keratin, gluten, shellac, gelatin and alginic acid hardened with formaldehyde or glutaraldehyde. In particular, an ammonio methacrylate copolymer is a material for the shell and/or for the trigger mechanism.

In a preferred embodiment of the pharmaceutical dosage form according to the present invention the dosage form, in particular the capsule device, comprises a wick system, in particular a capillary system, that is adapted to direct fluid into the dosage form by capillary forces.

Such a wick system advantageously allows a, preferably predetermined and/or controlled, entry of a fluid out of a tissue, in particular by capillary forces, into the dosage form, in particular into an inner space of the shell, by the capillary action of the wick system.

In a preferred embodiment of the pharmaceutical dosage form according to the present invention the dosage form, in particular the capsule device comprises a wick system.

The provision of the preparation in a compact condition advantageously makes it possible to provide a relatively small dosage form, in particular for rectal, oral or vaginal application, wherein the surface area of the sheet like preparation may be particularly advantageously increased by an expansion or the sheet like preparation, in particular for the active ingredient release at the predetermined site of action.

In a preferred embodiment of the pharmaceutical dosage form according to the present invention, the capsule device comprises a first tube element and at least a second tube element, wherein the second tube element has a smaller tube diameter than the first tube element. Preferably, the capsule device is formed by at least one first and/or at least one first and at least one further tube element.

In a preferred embodiment of the pharmaceutical dosage form according to the present invention a capsule device comprises a first tube element and at least a second tube element, wherein the second tube element has smaller tube diameter than the first tube element, and wherein the second tube element is at least partially arranged respectively inserted into the first tube element.

In a preferred embodiment of the pharmaceutical dosage form according to the present invention, the capsule device comprises a first half-cylinder element and at least a second half-cylinder element, wherein the second half-cylinder element has a smaller diameter than the first half-cylinder element. Preferably, the capsule device is formed by at least one first and/or at least one first and at least one further half-cylinder element. A half cylinder element is understood to be the half of a hollow-cylindrical part, which is obtained by cutting the cylinder along its symmetry-axis (central length axis) in two equal halfs.

In any case, a tube element or half-cylinder element may include a front face, which closes the tube/the half-cylinder part.

In a preferred embodiment of the pharmaceutical dosage form according to the present invention the preparation is a wafer.

In particular, the strip-like preparation of a dosage form according to the invention can be formed as a so-called wafer. Such a wafer can fit to the irregular surface contour of a predetermined site of action, in particular of a mucous membrane, for example of the intestinal, rectal or vaginal wall, after absorption of moisture. Additionally, a strip-like preparation of a dosage form according to the invention may be gellable or swellable.

In a preferred embodiment the strip-like preparation of a dosage form according to the invention is already flexible and stretchable before it is released out of the shell and can absorb a fluid entering the shell, e.g. from the administration process or inside the gastrointestinal tract.

In a preferred embodiment of the pharmaceutical dosage form according to the present invention the thickness of the strip-like preparation is 0.01 mm to 2 mm, preferably 0.03 mm to 1 mm, preferably 0.05 mm to 0.75 mm, preferably 0.05 mm to 0.5 mm, preferably 0.05 mm to 0.2 mm, preferably 0.08 mm to 0.15 mm, or 0.1 to 0.12 mm.

In particular, this is beneficial to provide a strip-like preparation with a relatively small thickness.

In a preferred embodiment of the pharmaceutical dosage form according to the present invention the strip-like preparation has an area between 0.5 and 25 cm$^2$, preferably between 1 to 10 cm$^2$.

In a preferred embodiment of the pharmaceutical dosage form according to the present invention the string-like or strip-like, in particular film shaped, foil shaped or wafer shaped, preparation, that comprises the active pharmaceutical ingredient, contains an active pharmaceutical ingredient in an amount know to be effective for the condition to be treated and depend upon site of administration and active ingredient. For e.g. budesonide the concentration/amount within the dosage form is significantly higher compared to mometasone containing dosage forms.

In a preferred embodiment of the pharmaceutical dosage form according to the present invention the string-like or strip-like, in particular film shaped, foil shaped or wafer shaped, preparation comprising the active pharmaceutical ingredient has a single-layered or multi-layered structure out of a single or multiple layers, wherein at least one (preferably first) layer contains an active pharmaceutical ingredient.

It is to be understood, that such a first layer containing the active pharmaceutical ingredient may be any layer of a multi-layered preparation with regard to its arrangement and that it is, in particular, not limited to an outer, inner, bottom or upper layer.

In a preferred embodiment of the pharmaceutical dosage form according to the present invention the string-like or strip-like, in particular film shaped, foil shaped or wafer shaped, preparation, that comprises the active pharmaceutical ingredient, comprises a multi-layered structure of multiple layers, wherein at least a first layer contains a first active pharmaceutical ingredient and wherein at least a further layer contains at least a further active pharmaceutical ingredient.

It is also within the scope of the present invention that the active pharmaceutical ingredient contained in a first layer is equal to or different from an active pharmaceutical ingredient contained in a further layer. In particular, a strip-like preparation of a dosage form according to the invention can be embodied as a so-called combination wafer and can contain a combination of active pharmaceutical ingredients of at least two active pharmaceutical ingredients in one or more layers individually or jointly.

In a preferred embodiment of the pharmaceutical dosage form according to the present invention the string-like or strip-like, in particular film shaped, foil shaped or wafer shaped, preparation comprising the active pharmaceutical ingredient comprises at least a first layer containing the active substance and/or a further layer containing the active substance, wherein the first layer containing the active substance and/or the further layer containing the active substance comprises a polymer, preferably a film forming polymer.

Such a layer comprising a polymer, preferably a film forming polymer advantageously serves as an active ingredient reservoir, wherein such a layer can release the active pharmaceutical ingredient under the effect of a fluid.

In a preferred embodiment of the pharmaceutical dosage form according to the present invention the string-like or strip-like, in particular film shaped, foil shaped or wafer shaped, preparation comprising the active pharmaceutical ingredient comprises at least one first layer containing the active ingredient and/or a further layer containing the active ingredient.

In a preferred embodiment of the pharmaceutical dosage form according to the present invention the string-like or strip-like, in particular film shaped, foil shaped or wafer shaped, preparation comprising the active pharmaceutical ingredient comprises at least a first layer containing the active ingredient and/or a further layer containing the active ingredient, wherein the at least one first layer containing the active ingredient and/or the further layer containing the active ingredient is an adhesive layer.

In a preferred embodiment of the pharmaceutical dosage form according to the present invention the at least one first layer containing the active ingredient and/or the further layer containing the active ingredient comprises a polymer, preferably a film forming polymer, wherein the polymer is a film forming polymer that is water dispersible and/or decomposable and/or water disintegrable.

A polymer for a first layer containing an active substance and/or for a further layer containing an active substance may, in particular, be selected from a group comprising polyvinyl alcohols, Polyvinylpyrrolidone, polyvinyl acetate, polyethylene glycol, polyethylene oxide polymers, polyurethanes, polyacrylic acids, polyacrylates, polymethacrylates, poly (methyl vinyl ether-maleic acid anhydrides), starch, starch derivates, natural gums, alginates, pectins and gelatin, Pullulan, gel forming proteins, Chitosan, Agar-Agar, agarose, carrageenan, xanthan, tragacanth, dextran, and cellulose ethers such as ethyl cellulose, hydroxyethyl cellulose, propyl cellulose, carboxymethyl cellulose, sodium-carboxy methylcellulose, hydroxypropyl cellulose, hydroxypropyl methylcellulose, hydroxypropyl ethyl cellulose, cellulose acetate, povidone and copovidone.

The polymers may be used individually or in a combination with each other in order to manufacture a sheet like preparation for the dosage form according to the invention with the desired properties as adhesion, release or disintegration properties. In particular, a string-like or strip-like preparation according to the invention can consist of a single polymer layer. Also, a sheet like preparation for a dosage form according to the invention may have a structure with two or multiple layers, when at least one of the layers contains an active pharmaceutical ingredient. If multiple layers contain the active pharmaceutical ingredient or the active pharmaceutical ingredients, they may differ from each other in their active ingredient content and in their combination of active ingredients, but also in their polymer composition and thus their adhesion and/or decomposition properties.

In a preferred embodiment of the pharmaceutical dosage form according to the present invention the string-like or strip-like, in particular film shaped, foil shaped or wafer shaped, preparation comprising the active pharmaceutical ingredient comprises at least one first active ingredient free layer, that does not contain an active pharmaceutical ingredient.

In a preferred embodiment of the pharmaceutical dosage form according to the present invention the string-like or strip-like, in particular film shaped, foil shaped or wafer shaped, preparation comprising the active pharmaceutical ingredient comprises at least a further active ingredient free layer that does not contain an active pharmaceutical ingredient.

In a preferred embodiment of the pharmaceutical dosage form according to the present invention the first active ingredient free layer and/or the at least one further active ingredient free layer is a water insoluble layer which preferably comprises water insoluble substances selected from the group ethyl cellulose and/or combinations of ethyl cellulose with other water insoluble substances, hydrophobic plasticizers, especially triethyl citrate, and/or dies and/or fragrances and/or flavorings.

In particular, the use of ethyl cellulose may be beneficial due to its properties comprising a good processability, biocompatibility, and water insolubility.

In a preferred embodiment of the pharmaceutical dosage form according to the present invention the first active ingredient free layer and/or the at least one further active ingredient free layer is an adhesive layer that preferably comprises hydroxypropyl methylcellulose.

The adhesive layer may vary in its desired thickness. Additionally or alternatively, the adhesive layer may be a mucoadhesive polymer selected from the group comprising cellulose derivates, starch and starch derivates, polyvinyl alcohol, polyethylene oxide, polyethylene, polypropylene, polyacrylic acid and polyacrylate derivates, Polyvinylpyrrolidone, Povidone, Copovidone, Sodium alginate, gelatin, Xanthan gum, Carrageenan, pectins, dextrans, lectins, Chitosan, Pullulan, and mixtures thereof.

The adhesive layer may vary in its desired thickness. Additionally or alternatively, the adhesive layer may comprise a solvent that is selected from the group comprising water, Ethanol, Methanol, Acetone, organic solvents, and mixtures thereof.

Furthermore, the adhesive layer may additionally contain additives such as colorants, fragrances, flavoring agents, preservatives, antioxidants, penetration enhancers, solubilizers, disintegration accelerators, pore formers, lubricants, and mixtures thereof.

In a preferred embodiment of the pharmaceutical dosage form according to the present invention the string-like or strip-like preparation has a multi-layered structure, preferably with two or three layers, and comprises at least one layer containing an active substance and at least one active ingredient free layer.

In a preferred embodiment of the pharmaceutical dosage form according to the present invention the string-like or strip-like preparation comprises a multi-layered structure, preferably with three layers, wherein a first layer containing an active ingredient and/or a further layer containing an active ingredient is arranged between a first active ingredient free layer and/or a further active ingredient free layer, wherein, preferably, the first active ingredient free layer is a water insoluble layer, that preferably comprises ethyl cellulose, and the at least one further active ingredient free layer is an adhesive layer, that preferably comprises hydroxypropyl methylcellulose.

A drug according to the present invention, in particular a string-like or strip-like preparation, may additionally contain one or more additives. In particular, the following substances are eligible as additives: lubricants, lubricants, glidants, binders, additional active ingredients, disintegrants, antioxidants, chelating agents, coating agents, flow agents, preservatives, fillers, surfactants, plasticizers, and pigments. Furthermore, the additives may be selected from the following group: pore formers, penetration enhancers, solubilizers, emulsifiers, comprising polyethoxylated sorbitan fatty acid esters, ethoxylated fatty alcohols, and lecithin; plasticizers, comprising polyethylene glycol, glycerol and other polyhydric alcohols, higher alcohols such as dodecanol, undecanol, or octanol, sorbitol, mannitol and other sugar alcohols, dexpanthenol and triglycerides; fillers comprising highly disperse silicon dioxide, titanium dioxide, zinc oxide, chalk and starch; colorants; sweetening and flavoring agents; wetting agents; preservatives; pH regulators and antioxidants; disintegration accelerators; permeation enhancers which improve the resorption of estradiol into the mucous membrane, for example, fatty acids and fatty acid esters, polyhydric alcohols such as propanediol, tocopherols or essential oils such as menthol.

The fraction of these additives may be up to 60% by weight relative to the total weight of the sheet like preparation. Preferably, the fraction of the additives is between 5 and 40% by weight. By adding one or more of said additives, the person skilled in the art can specifically influence the chemical and physical properties of the film shaped drug containing the active ingredient such that, for example, a desired flexibility, adhesivity, swellability or decomposability as well as diffusion properties may be adjusted.

According to a preferred embodiment the pharmaceutical dosage form, in particular the string-like or strip-like preparation, according to the invention is intended to enable a time delayed active ingredient release. The active pharmaceutical ingredient is preferably released over a period of 4 hours, preferably over a period of 6 hours and most preferably over a period of 8 hours. In order to achieve a delayed active ingredient release in case of two-layered or multi-layered preparations, at least one of the layers containing an active ingredient, in particular a polymer layer, has a delayed active ingredient release. For a delayed active ingredient release the film shaped medicaments are preferably formulated as slowly soluble or slowly disintegrating film which are completely disintegrated or dissolved only after several hours. Preferably, they are completely disintegrated or completely dissolved only after 4 hours, preferably only after 6 hours, and even most preferably only after 8 hours or even only after more than 24 hours.

According to an alternative preferred embodiment the pharmaceutical dosage form according to the invention, in particular the string-like or strip-like preparation is a rapidly releasing dosage form which releases the active pharmaceutical ingredient within 1 hour, preferably within 30 minutes, and even most preferably within 5 minutes. For a rapid active ingredient release the film shaped preparation may preferably be formulated as a fast dissolving or rapidly disintegrating film. The sheet like preparation is adapted to essentially completely disintegrate, to transition to a gelatinous state or to dissolve preferably within a few minutes after the release. Preferably, the sheet like preparation is completely disintegrated, transitioned into a gel state or completely dissolved within 1 hour, preferably within 30 minutes, more preferably within 15 minutes, and particularly most preferably within 5 minutes.

According to a preferred embodiment the film shaped medicaments according to the invention are adhesive, in particular mucoadhesive. An embodiment that comprises only an adhesive, in particular mucoadhesive surface, is particularly preferred. Thereby, a sticking of the drug formulation to a predetermined site of action, in particular a mucous membrane, during the application duration is achieved and the active pharmaceutical ingredient or the active pharmaceutical ingredients can be resorbed directly at a predetermined site of action, in particular through a mucous membrane.

Furthermore, a string-like or strip-like preparation may comprise a layer at a side that is opposed to the adhesive, in particular mucoadhesive surface, wherein said layer is impermeable for the active pharmaceutical ingredient such that at the application at a predetermined site of action a directed active ingredient release can be achieved.

The pharmaceutical dosage form, in particular the string-like or strip-like preparation, can be prepared by a person skilled in the art by basically known methods, for example by coating of an inert support with a liquid composition which comprises the polymer(s), active pharmaceutical ingredient(s) and optionally additive(s) and solvent(s), by means of e.g. a method involving a doctor blade, spray processors or extrusion processors. The thin film layer obtained in such a way is dried. For a multi-layered sheet like preparation one or more coatings may be applied onto the existing film layer in the same manner or may be manufactured separately and then be subsequently laminated.

A pharmaceutical dosage form, in particular the capsule device and/or the string-like or strip-like preparation, may further comprise at least one taste-masking additive. This advantageously allows the masking of a bitter or in some other way unpleasant tasting active pharmaceutical ingredient but may also be beneficial to accelerate the onset of effect of an active pharmaceutical ingredient. Taste-masking additives are known to the person skilled in the art. Such a taste-masking additive may, in particular, comprise a sugar alcohol selected from mannitol, sorbitol, xylitol, malitol, lactitol, erythritol, threitol, and isomalt as well as sodium hydrogen carbonate.

An active pharmaceutical ingredient contained in a string-like or strip-like preparation of the pharmaceutical dosage form according to the invention may, in particular, be selected from the group comprising proteins and peptides, in particular insulin, buserelin, oesmospressin, calcintonin and estrogen as well as biotechnologically manufactured drugs such as the antibody rituximab. Here, it is to be understood that proteins and peptides, in particular insulin, buserelin, oesmopressin, calciotonin and estrogen may display, under certain circumstances, a bad—in particular a bad oral—bioavailability and thus are good candidates for the application by means of the dosage form according to the present invention.

Substances from the following groups are particularly suited as active pharmaceutical ingredients: drugs acting on the skeleton and the muscles, drugs acting on the nervous system, hormones and drugs acting on the hormonal system, gynecologic acting drugs, drugs acting on the cardio-vascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides.

In particular, the string-like or strip-like preparation may comprise at least a first region and at least a second region, wherein the at least one first region comprises the active pharmaceutical ingredient. Preferably, the at least one second region comprises a further active pharmaceutical ingredient that is different from the active pharmaceutical ingredient of the at least one first region of the sheet like preparation. Also preferably, the at least one second region does not comprise the active pharmaceutical ingredient of the at least one first region of the sheet like preparation. Alternatively and preferably, the at least one second region comprises the active pharmaceutical ingredient of the at least one first region of the sheet like preparation with a concentration by area, volume or mass that is different from the concentration of the active pharmaceutical ingredient of the first region.

It is to be understood, that in this context active pharmaceutical ingredients may also refer to mixtures of active pharmaceutical ingredients and/or additives. Thus, the at least one second region of the sheet like preparation may comprise a mixture that differs from the mixture of the at least one first region. In particular, the mixtures of the at least one first region and of the at least one second region may differ in the composition of active pharmaceutical ingredients and/or additives as well as in the amount of the respective active pharmaceutical ingredients and/or additives.

In particular, this advantageously allows releasing different active pharmaceutical ingredients to different regions of the body, in particular to different mucous membranes or to different regions of a mucous membrane such as gastrointestinal, buccal, oral, esophageal, gastric, intestinal, rectal or vaginal mucosa, with a single pharmaceutical dosage form. Preferably, one active pharmaceutical ingredient or one mixture of active pharmaceutical ingredients can be applied to a first region of the vaginal mucosa that is closer to the cervix than a second region of the vaginal mucosa and another active pharmaceutical ingredient or another mixture can be applied to said second region. Moreover, no active pharmaceutical ingredients may be released to the first or the second region of the vaginal mucosa. Alternatively and preferably, the first region of the sheet like preparation may be in contact with an esophageal mucosa and the second region of the sheet like preparation may be contact with a buccal mucosa. In this way, the esophageal mucosa can be treated with the active pharmaceutical ingredient while the buccal mucosa is treated with another active pharmaceutical ingredient, not treated or an additive is released to the buccal mucosa. In particular, a flavoring agent and/or a local anesthetic may be released, particularly to increase or decrease the production of saliva and/or to make the application of the pharmaceutical dosage form more pleasant and/or to suppress the urge to gag.

In a preferred embodiment of the pharmaceutical dosage form according to the present invention, in which the string-like or strip-like preparation comprises at least a first region and at least a second region, the second region may comprise a further active pharmaceutical ingredient that counteracts the active pharmaceutical ingredient of the first region. This may be beneficial to suppress a systemic effect of the active pharmaceutical ingredient of the first region. In particular, a fluid that passes along the mucous membrane may pass, at first, the first region and then the second region, and therefore may, at first, take up the active pharmaceutical ingredient of the first region, which is then counteracted, preferably neutralized, by the further active pharmaceutical ingredient of the second region. In particular, such an active pharmaceutical ingredient counteracting the other pharmaceutical ingredient can be chosen from the following list: enzymes that break down active pharmaceutical ingredients such as esterases; ions that form complexes with the other active pharmaceutical ingredient such as calcium, iron or magnesium; sympathomimetic drugs and sympatholytic drugs; parasympathomimetic drugs and parasympatholytic drugs; antibodies that bind drugs; drugs to treat the side effects of the other active pharmaceutical ingredient without counteracting the effect of the other active pharmaceutical ingredient. Additionally or alternatively, the sheet like preparation may comprise, in a similar manner, a first layer with the active pharmaceutical ingredient and a second layer with the further active pharmaceutical ingredient that counteracts the active pharmaceutical ingredient of the first layer. In this case, the above mentioned advantages may be achieved, wherein the effect of the active pharmaceutical ingredient of the first layer is directed in the direction of the mucous membrane or away from it.

A preferred embodiment of the pharmaceutical dosage form according to the present invention is adapted for the application to an upper gastrointestinal tract such as throat, esophagus, cardia and/or stomach, and particularly to the respective mucous membranes and/or preferably to a buccal and/or esophageal mucosa.

A preferred embodiment of the pharmaceutical dosage form according to the present invention is adapted for the application to a nasopharyngeal mucosa.

In a preferred embodiment of the pharmaceutical dosage form according to the present invention, in particular a dosage form for the application to a buccal and/or esophageal mucosa, the shape of the dosage form or a part of the dosage form, in particular the shell, is such that can be swallowed.

In particular, a shell with the shape of a capsule device can be swallowed. Preferably, the circumference of the capsule device measured in a plane perpendicular to the length axis A, is shorter than 6 cm, preferably shorter than 3 cm, and preferably shorter than 2 cm, as well as longer than 0.2 cm, preferably longer than 0.5 cm, and preferably longer than 1 cm. Preferably, the length of the capsule device measured along the longitudinal axis A of the capsule device is shorter than 5 cm, preferably shorter than 3 cm, and preferably shorter than 2 cm, as well as longer than 0.5 cm, preferably longer than 1 cm, and preferably longer than 1.5 cm. In particular, the capsule device may have a shape according to a standard capsule form such as 00, 0, 1 or 3, which have a length along the longitudinal axis A between 16.1 mm and 23.5 mm and a circumference between 17.9 mm and 26.7 mm. In a similar manner the pharmaceutical dosage form or the part of the pharmaceutical dosage form to be swallowed may be shaped. Furthermore, a smooth and/or glidable surface of the shell, the dosage form or the part of the dosage form may be beneficial to facilitate the swallowing.

This advantageously allows an oral administration of the pharmaceutical dosage form according to the invention. In particular, only the dosage form or the part of the dosage form, preferably the shell, with the suitable shape is swallowed. In this context it is to be understood, that parts of the dosage form may be adapted to be swallowed while other parts of the dosage form may not be adapted to be swallowed.

In a preferred embodiment of the pharmaceutical dosage form according to the present invention, in particular a dosage form for the application to a buccal and/or esophageal mucosa, a nasopharyngeal mucosa, a gastrointestinal mucosa, a rectal mucosa or a vaginal mucosa, the sheet like preparation comprises at least one active pharmaceutical ingredient (the drug name also includes any pharmaceutically acceptable salt thereof) selected from the group: diagnostics substances such as dyes or stains, analgesics, preferably NSAIDs, such as ibuprofen or flurbiprofen; local anesthetics such as benzocaine, butamben, dibucaine, lidocaine, oxybuprocaine or novocaine; antibiotics such as penicillin, amoxicillin or vancomycin; antiseptics such as 2,4-dichlorobenzyl alcohol, amylmetacresol or cetylpyridinium chloride; steroids such as corticosteroids, glucocorticoids, fluticasone, budesonide, clocortolone, perdesonide, hydrocortisone, clobetasonbutyrate, flumetason, flupredniden, hydrocortisone aceponate, hydrocortisone buteprate, hydrocortisone-17-butyrate, triamcinolonacetonid, amcinoid, betamethason-17,21-dipropionate, betamethason-17-valerate, desoximetasone, diflucortolon-21-valerate, fluocinolonacetonid, fluocinonid, fluticason-17-propionate, methylprednisolone aceponate, mometasonfuroat, pednicarbat or clobetasol-17-propionate; parasizides, which are also called parasiticides, such as mebendazole, albendazole, tiabendazole, diethylcarbamazine, diaminodiphenyl sulfone, benznidazole, ivermectin, pyrantel, praziquantel; fungicides such as nystatin, imidazole, triazole, thiazole, clotrimazole, ketoconazole or undecylenic acid; hexamethyl pararosaniline chloride, Amphotericin B, botulinum toxin, sucralfat, nitric oxide or nitric oxide forming agents such as isosorbide dinitrate or nitroglycerine, furanocoumarins, benzoic acid, citric acid, lactic acid, pH buffers, antacids, calcium carbonate, magnesium carbonate or aluminum carbonate. Additionally or alternatively, the sheet like preparation particularly can comprise an inflammation regulator such as montelukast, interleukin receptors or interleukin antibodies. Additionally or alternatively, the sheetlike preparation particularly can comprise beclomethasone dipropionate, budesonide or ciclesonide, which are particularly beneficial for asthma therapy. Additionally or alternatively, the sheetlike preparation particularly can comprise mesalazine, sulfasalazine or olsalazine, which are particularly beneficial for treating inflammatory bowel disease.

In one embodiment, the active ingredient is selected among corticosteroids. Exemplarily budesonide, mometasone, fluticasone and ciclesonide, and pharmaceutically acceptable salts thereof are to be mentioned. As to the conditions to be treated exemplarily those related to the gastrointestinal mucosa, preferably the esophagus, such as GERD, NERD as well as eosinophilic esophagitis are to be mentioned.

In particular, the string-like or strip-like preparation comprising a specific active pharmaceutical ingredient advantageously allows, preferably locally, treating a respective disease or infection. Thus, a specific active pharmaceutical ingredient may be applied to a respective application site, in particular a mucosa, and the local concentration and/or the therapeutic effect may be increased and/or side effects, in particular adverse reactions, may be reduced compared to a systemic application. In this context it is to be understood, that besides the local effect also a systemic effect may be possible, preferably by the uptake of the active pharmaceutical ingredient through the mucous membrane into the body. Moreover, in a preferred embodiment the sheet like preparation may comprise different active pharmaceutical ingredients, wherein at least one active pharmaceutical ingredient is chosen such that it remains, at least essentially, localized at and/or within the mucous membrane while at least another active pharmaceutical ingredient is chosen such that it enters the body through the mucous membrane, thus in particular causing a systemic effect.

A preferred embodiment of the pharmaceutical dosage form according to the present invention is adapted to be orally administered. Therefore, the dosage form or a part of the dosage form, in particular the capsule device, is shaped a swallowable manner. Preferably, this dosage form is formed as described above. Furthermore, this preferred embodiment may comprise a drug as the active pharmaceutical ingredient or active pharmaceutical ingredients that is traditionally unsuitable for oral administration, in particular due to a small bioavailability, highly variable intra- or inter-individual plasma levels, degeneration or deactivation of the drug by digestive secretions and enzymes, dilution effects by intestinal fluids, poor resorbability, a high first pass effect and/or a very short length of stay at the absorption window. Among these drugs are, for example: proteins and peptides such as insulin, buserelin, calcitonin or desmopressin which is also called oesmopressin; hormones such as estrogen; as well as biotechnologically produced drugs such as antibodies, in particular rituximab.

In a preferred embodiment of the pharmaceutical dosage form according to the present invention, in particular a dosage form for the application to a buccal, intestinal, rectal or vaginal mucous membrane, the string-like or strip-like preparation provides, after its release by the release mechanism, a relatively large surface area. In particular, the sheet like preparation is adapted to come into contact with a relatively large surface area, preferably of the mucous membrane, preferably at the predetermined site of release or site of action, after its release by the release mechanism. Consequently and preferably, the sheet like preparation can cover a relatively large surface area of the mucous membrane, in particular relatively large in comparison to the volume of the sheet-like preparation and/or to the amount of active pharmaceutical ingredients. Some particular advantages have already been described above. In particular, an enhanced resorption of the active pharmaceutical ingredient contained in the sheet like preparation can be realized. Moreover in a preferred variant of this embodiment, in particular with a sheet like preparation with multiple layers, the release of the active pharmaceutical ingredient can be directed into the mucous membrane. Thus, the local concentration of the active pharmaceutical ingredient and/or the bioavailability and/or the rate of absorption and/or the local effect may be increased. Furthermore, the concentration of the active pharmaceutical ingredient in the fluids that are present near the mucous membrane may be decreased by a directed release, and therefore side effects may be reduced and/or the bioavailability and/or the local effect may be increased.

The term "relatively large" as used herein preferably refers to one thing being a larger than another thing and/or one thing being larger than such a thing or corresponding quantity would be in a traditional embodiment of this thing, wherein preferably the extent, spatial extent, length, area, volume, surface area, cross-sectional area, enveloping cross-sectional area, contact area, covering area, diameter, circumference, path length, size, amount, quantity, scope, capacity and/or average size or scope is larger by a factor of preferably at least 125%, preferably at least 200%, preferably at least 500%, preferably at least 1000%, and preferably at least 5000%. In particular, a relatively large surface area of a sheet like preparation according to the present invention is larger than the surface area of a traditional dosage form or its preparation. In particular, the surface area of a sheet like preparation according to the present invention can be relatively large in comparison to the volume of the sheet like preparation. In particular, an area, preferably surface area, can be compared with a corresponding volume. Preferably, an area is relatively larger than a volume, if the square root of the area is larger than the cube root of the volume, preferably by a factor of at least 125%, preferably at least 200%, preferably at least 500%, preferably at least 1000%, and preferably at least 5000%. Additionally or alternatively, a relatively large surface area of a sheet like preparation preferably refers to a surface area of the sheet like preparation that is larger than the surface area of a traditional dosage form or its preparation with the same amount of an active pharmaceutical ingredient, preferably by the above given factors. It is to be understood, that the surface area of the sheet like preparation is an, at least essentially, uninterrupted surface area, while, in particular, a powder may also comprise a large surface area that is, however, not an essentially closed surface, but rather a huge number of small surface areas of the individual particles of the powder. In particular, mutatis mutandis, this also holds true for a drug or an active pharmaceutical ingredient that is dissolved in a fluid. Especially, a contact with a relatively large surface area, in particular of a mucosa, means that the contact area and/or the area that is covered, in particular by a sheet like preparation, is larger than the area which would be in contact and/or covered by a traditional dosage form or its preparation. Especially, if the traditional dosage form would dissolve in a fluid, then this fluid may have a large contact area with their respective mucous membrane, but the surface area would not be an essentially uninterrupted surface area, as described above, and/or the concentration of the drug or active pharmaceutical ingredient in said fluid may be lower than the concentration in the sheet like preparation and/or or in the mucous membrane covered by the sheet like preparation and/or in a fluid filled gap between the sheet like preparation and the covered area of the respective mucous membrane.

Specifically, an esophagus can be treated with an active pharmaceutical ingredient that is locally applied to its mucous membrane. So, in particular, the active pharmaceutical ingredient can be applied to an extended region of the mucous membrane of the esophagus. Moreover, the active pharmaceutical ingredient may act locally to the mucous membrane of the esophagus. Therefore, side effects due to systemic effect of the active pharmaceutical ingredients may be reduced and/or the local effect to the mucous membrane of the esophagus, in particular due to the locally increased concentration of the active pharmaceutical ingredient, may be enhanced. Moreover, when the sheet like preparation releases the active pharmaceutical ingredient locally and/or over a prolonged time, the therapeutic response may be improved, and in particular the local effect of the active pharmaceutical ingredient can be increased.

Furthermore, in particular due to the spatially extended region of action, the necessity for a systemic administration may be reduced. Even more specifically, esophagitis, particularly eosinophilic esophagitis, can be treated by such a pharmaceutical dosage form. Here, a drug, in particular the active pharmaceutical ingredient, may target the mucous membrane of the esophagus and/or may preferably be selected from the group comprising: steroids such as corticosteroids, glucocorticoids, fluticasone, budesonide, clocortolone, perdesonide, hydrocortisone, clobetasonbutyrate, flumetason, fluprediden, hydrocortisone aceponate, hydrocortisone buteprate, hydrocortisone-17-butyrate, triamcinolonacetonid, amcinoid, betamethason-17,21-dipropionate, betamethason-17-valerate, desoximetasone, diflucortolon-21-valerate, fluocinolonacetonid, fluocinonid, fluticason-17-propionate, methylprednisolone aceponate, mometasonfuroat, pednicarbat or clobetasol-17-propionate; nitric oxide or nitric oxide forming agents such as isosorbide dinitrate or nitroglycerine, beclomethasone dipropionate, ciclesonide, pH buffers, antacids, calcium carbonate, magnesium carbonate or aluminum carbonate. Additionally or alternatively, the sheet like preparation particularly can comprise an inflammation regulator such as montelukast, interleukin receptors or interleukin antibodies.

In a preferred embodiment of the pharmaceutical dosage form according to the present invention, in particular a dosage form for the application to a buccal and/or esophageal mucosa and/or to a nasopharyngeal mucosa, the release mechanism comprises a string member, wherein the string member is expandable from a compact form to an expanded form. In particular upon activation of the release mechanism, the string member can expand or can be expanded by a pulling movement and/or force. Preferably, the string member comprises the string-like or strip-like preparation or is connected to an end portion of the string-like or strip-like preparation. The string member may comprise the string-like or strip-like preparation in the compact form and/or in the expanded form. Alternatively and preferably, the string-like or strip-like preparation may be adapted to form the string member. Thus, the string member contains the active pharmaceutical ingredient. It is to be understood, that the string member may only partially comprise the string-like or strip-like preparation or that the string-like or strip-like preparation may only partially form the string member. Furthermore, only a part of the string member may convert from a compact form to an expanded form, while at least one other part of the string member remains in a compact form or an expanded form.

The term "compact form" as used herein preferably refers to a folded form, coiled form, rolled form, coiled up form or collapsed form. In particular, a string-like or strip-like preparation has a smaller spatial extent and/or exposes a smaller amount of its surface in a compact form than in a form that is not a compact form, particularly in an expanded form. Preferably, a string-like or strip-like preparation in a compact form is folded, collapsed, coiled, rolled, coiled up, compressed, lumped together or brought into a smaller format in another way. In particular, a string-like or strip-like preparation can have a predetermined size or spatial extent, when it is in a compact form.

The term "expanded form" as used herein preferably refers to an unfolded form, spread out form, opened up form, elongated form, stretched form or oblong form. In particular, a string-like or strip-like preparation has a greater spatial extent and/or exposes a greater amount of its surface in an expanded form than in a form that is not an expanded form, particularly in a compact form. Preferably, a string-like or strip-like preparation in an expanded form is unfolded, spread out, opened up, unrolled, uncoiled, opened, elongated, stretched, expanded or brought into a bigger format in another way. In particular, a string-like or strip-like preparation can have a predetermined size or spatial extent, when it is in an expanded form. Alternatively, the size or spatial extent of a string-like or strip-like preparation may depend on the conditions present and a site of action or application site, and thus may not be predetermined.

The string member advantageously allows releasing the active pharmaceutical ingredient, in particular to mucous membranes that enclose a rather small lumen or cavity such as the esophagus or nasal cavity. Furthermore, the compact form of the string member advantageously makes it possible to provide a relatively small pharmaceutical dosage form, in particular for oral administration, which facilitates swallowing the dosage form. Additionally, the string member may expand, in particular unfold, uncoil, unroll, stretch or elongate, to the expanded form, and thus enable the release of the active pharmaceutical ingredient to an elongated region of a mucous membrane, in particular a buccal and/or esophageal mucosa and/or a nasopharyngeal mucosa. In particular, it is beneficial that the exposed surface area and/or the length of the string member or of the sheet like preparation exposed to the environment, in particular the mucous membrane, is increased, when the string member expands, particularly elongates or stretches, from the compact form to the expanded form. By this advantageous way, the active pharmaceutical ingredient is protected in the compact form and/or the release of the active pharmaceutical ingredient is enhanced by a rather large and/or long contact area in the expanded form. An advantage of a preferred variant of this embodiment is the use of the string member to support and/or to transport the sheet like preparation, and thus particularly making it possible to choose different substances and compositions for the sheet like preparation. Another advantage of an alternative and preferred variant results from the fact that the sheet like preparation forming the string member, and thus particularly making it possible to reduce the number of components of the dosage form and preferably to simplify the manufacturing of the release mechanism and/or the sheet like preparation.

In a preferred embodiment of the pharmaceutical dosage form according to the present invention the string-like preparation, in particular in an expanded form, is string shaped, cord shaped or tube shaped. Preferably or alternatively, the string-like or strip-like preparation is bendable.

In a further refined or alternate preferred embodiment of the pharmaceutical dosage form according to the present invention, the strip-like preparation is adapted to form, in particular in an expanded form, a string, cord, strip or tube. Preferably, the string-like or strip-like preparation is bendable such that it can convert from a compact form, in particular with a folded, collapsed, coiled, rolled or coiled up sheet like preparation that may preferably have a string like, cord like, strip like or tube like shape, to the expanded form.

In particular, this advantageously allows the application of the dosage form and the release of the string-like or strip-like preparation to a mucous membrane that embraces a rather small lumen, in particular with a small diameter, and/or the treatment of a mucous membrane or an organ with a mucous membrane that shows an adverse effect when larger regions of it are covered or its lumen or a part of it is obturated by the string-like or strip-like preparation. Specifically, such an adverse effect can be a gag reflex, a sneeze stimulus or the blockage of fluid such as liquid, water, intestinal fluids or air. Another advantage is a possibly simplified manufacture. Additionally and preferably, the spatial extent of the expanded form, in particular the length of the string-like or strip-like preparation in its expanded form, in particular along its longitudinal and/or elongation axis, can be substantially larger than the spatial extent of the compact form, in particular the maximum diameter of the sheet like preparation in its compact form. The term "substantially larger" as used herein preferably refers to a ratio greater than or equal to 3:1, preferably 6:1, preferably 10:1, preferably 20:1, preferably 30:1, in particular with respect to an aspect ratio, an area ratio or a volume ratio. It is to be understood that it may also be beneficial to limit the maximum spatial extension and thus ratio to preferably 200:1, preferably 100:1, preferably 60:1, and preferably 40:1. In such a manner, in particular in a case where the volume of the string-like or strip-like preparation stays constant, a minimum diameter along a cross-section, which is, at least essentially, orthogonal to the longitudinal axis of the string-like or strip-like preparation in its expanded form, can be ensured. On the other hand, in case of a preparation that is, at least in its expanded form, shaped as a tube with a relatively larger diameter, preferably with a diameter that corresponds to the diameter of the respective lumen enclosed by the respective mucous membrane, the mucous membrane can be covered to a larger amount as compared to a preparation with a smaller diameter, e.g. a string shaped preparation.

In a preferred embodiment of the pharmaceutical dosage form according to the present invention the string-like or strip-like preparation, at least in the expanded form, is longer than 5 cm, preferably longer than 10 cm, preferably longer than 30 cm, and preferably longer than 40 cm, and preferably shorter than 95 cm, preferably shorter than 70 cm, and preferably shorter than 50 cm. In this context it is to be understood, that a dosage form, and in particular a string-like or strip-like preparation, that comprises at least one end adapted to be held during swallowing requires a length of the sheet like preparation that is correspondingly longer compared to the numbers given above, preferably by at least 5 cm, preferably by at least 10 cm, and preferably by at least 20 cm. Thus, such a sheet like preparation may preferably have length of, at least essentially, 60 cm.

In this context and/or the present invention, the term "length" or terms relating to length such as "longer" or "shorter" preferably refer to a length measured along the longitudinal and/or an expansion and/or an elongation axis of a respective object, in particular of the string-like or strip-like preparation. Specifically, the length of a string-like or strip-like preparation in its expanded form, preferably elongated form, may be measured with a tape measure. More specifically, the string-like or strip-like preparation may comprise a first end and a second end and the tape measure, in order to measure the length of the string-like or strip-like preparation, may be guided along the string-like or strip-like preparation from said first end to said second end. In particular, when the respective object, e.g. the string-like or strip-like preparation, follows, at least essentially, a straight line, the length of the respective object is the length along this line. Specifically, if this length is the longest spatial extent, the direction of said straight line corresponds to the longitudinal axis.

In a preferred embodiment of the pharmaceutical dosage form according to the present invention the string-like or strip-like preparation has an area and/or surface area between 0.5 and 25 cm$^2$, preferably between 2 to 25 cm$^2$, preferably between 5 to 25 cm$^2$, preferably between 5 to 15 cm$^2$, preferably larger than 0.5 cm$^2$, and preferably smaller than 40 cm$^2$. Preferably the ration of the length of the sheet like preparation and the width of the sheet like preparation is between 40:1 and 400:1, or preferably 60:1 and 300:1, or preferably 80:1 and 200:1. Said width can be an average width of a sheet like preparation, measured, for example, perpendicular to the length of the sheet like preparation. Said ratio can be a ratio of the length of the sheet like preparation and a circumference, in particular an average, of the sheet like preparation, wherein said circumference can be, for example, twice the width of a sheet like preparation in the case of a strip-shaped sheet like preparation.

In particular, this is beneficial for the application to a mucous membrane. Specifically, the mucous membrane of an esophagus can be covered and/or locally treated by such a strip-like preparation comprising the active pharmaceutical ingredient. It is to be understood, that depending on the specific embodiment of the dosage form that string-like or strip-like preparation may, at least partially and preferably to a substantially large extent, cover the mucous membrane of the esophagus and/or may extend, at least partially and preferably to a substantially large length, along the longitudinal axis of the esophagus. Therefore in a preferred variant, the active pharmaceutical ingredient can be released on an extended region of the esophageal mucosa, and thus this extended region can be treated. Moreover, in an alternate or refined preferred variant with a sheet like preparation that does not dissolve immediately, but preferably dissolves in a time controlled manner and/or adheres to the mucous membrane, the active pharmaceutical ingredient can be released over a prolonged time, and thus, in particular, the therapeutic effect may be improved.

Specifically, in case of an orally administered dosage form preferably for the application to the esophagus, the dosage form will be transported by an external movement, which may be the movement of the dosage form while it is swallowed. Therefore, the muscles of the esophagus generate a force that acts on the dosage form or a part of it. In particular, the mucous membrane of the esophagus can act directly on the dosage form and/or can act indirectly to the dosage form, preferably via a fluid, particularly a liquid such as a beverage, water or saliva, which is preferably swallowed together with the dosage form. Out of those movements forces or pressures may arise. From another point of view, forces and/or pressures of the esophagus, its mucous membrane and muscles may cause said movements.

In certain embodiments fixing the end portion of the preparation in the oral cavity can increase the user convenience. Furthermore, an end portion that is adapted to be fixed in the oral cavity may be manufactured in a simple, and thus cost efficient way, and/or may be particularly reliable, especially because the user may notice whether the end portion is properly fixed before continuing with the administering of the dosage form, e.g. swallowing the dosage form or a part of it. Similar advantages may arise for a holding device adapted to be held in a hand while administering of the dosage form.

In a preferred embodiment of the pharmaceutical dosage form according to the present invention, at least during the release of the string-like or strip-like preparation, the released portion of the string-like or strip-like preparation and the pharmaceutical dosage form move relatively to each other and thereby define a movement path of the dosage form. Additionally, when viewing in the direction of the movement path, the enveloping cross-sectional area of the dosage form is larger than the enveloping cross-sectional area of the string-like or strip-like preparation. In particular, the enveloping cross-sectional area of the dosage form can refer to the enveloping cross-sectional area of a swallowable part of the dosage form, preferably the capsule device. In particular, the enveloping cross-sectional area of the string-like or strip-like preparation can refer to the enveloping cross-sectional area of the released part of the string-like or strip-like preparation. It is to be understood, that these relations particularly hold true during the release of the string-like or strip-like preparation. In particular, the string-like or strip-like preparation may expand, and thus have a larger enveloping cross-sectional area than the dosage form afterwards. It is to be understood, that the above described relations are particularly important for the portion of the string-like or strip-like preparation that just has been released by the dosage form. Preferably, the length of this portion, measured along the movement path, is, at least essentially, as long as the length of the dosage form, measured along the movement path, preferably twice as long, preferably five times as long, and preferably twenty times as long. Particularly, the relation of enveloping cross-sectional areas can be reflected and/or correspond to the relation of the respective maximum diameters or minimum diameters, which follow the respective transverse axis or are, at least essentially, orthogonal to the respective longitudinal axis or direction of the movement.

This may advantageously allow facilitating the movement of the dosage form by swallowing it or by peristaltic movements. Certain variants of this embodiment can improve the user convenience and/or reduce the risk of injury. In particular, as at least a section of the released string-like or strip-like preparation that is next to the dosage form has a smaller cross-sectional area, such a dosage form is better a swallowable. Specifically, this tapering behind the dosage form helps the muscles of the esophagus to swallow the dosage form. Preferably, the dosage form, in particular the capsule device such as a capsule, also tapers at least in and/or against the direction of the intended movement path, and thus further facilitates swallowing it. Furthermore, the dosage form may be adapted such that its longitudinal axis is, at least essentially, parallel to the intended to movement path. Moreover, the dosage form may release the sheet like preparation against the direction of the intended movement path, e.g. at the rear side of the dosage form regarding to the intended movement path or movement of the dosage form.

In a preferred embodiment of the pharmaceutical dosage form according to the present invention the string-like or strip-like preparation has at least a first portion and a second portion with different enveloping cross-sectional areas, in particular when viewed in the direction of the movement path, wherein the portion that is released before the other portion may have a smaller cross-sectional area. In an alternate and preferred embodiment the sheet like preparation tapers from a second end of the string-like or strip-like preparation to the first end of the string-like or strip-like preparation, wherein the first end of the string-like or strip-like preparation is on the side of the string-like or strip-like preparation that is released first. In particular, for the application to the esophagus both embodiments result in a string-like or strip-like preparation that is, after its release, smaller in the upper region of the esophagus and the oral cavity and larger in the lower region of the esophagus. This may beneficially facilitate the swallowing the dosage form and/or increase the user convenience, in particular suppress or avoid a gag reflex. In a preferred variant the first portion is a string member.

It is to be understood, that the terms "pharmaceutical dosage form" and "dosage form" as used herein are preferably interchangeable. Preferably, a dosage form can have non-pharmaceutical applications. In particular, a dosage form can be used for the therapy and/or for the diagnosis of a disease.

It is to be understood, that certain embodiments of a pharmaceutical dosage form according to the present invention differ from a catheter in that they are, at least essentially, fully enclosed by the body of a user after the administration. Additionally or alternatively, the administration is performed without additional tools and/or without applying a force or movement that is external to the body of a user. However, an applicator for assisting swallowing the dosage form may be used for administration (cf. FIG. 9a to 9d). Preferably, a pharmaceutical dosage form according to the present invention can be administered by the user without professional help. This is particularly beneficial, if the dosage form is to be administered on a regular, in particular daily, basis. Furthermore, the user convenience may be improved, the safety may be increased and/or the risk of injury may be reduced. Especially, the convenient administration is also beneficial for the treatment of animals. Similarly it is to be understood, that a pharmaceutical dosage form according to the present invention is different from a stent. In particular, a stent does generally not comprise a trigger mechanism in the sense of the present invention. Moreover, the object of a stent generality is to keep open a hollow organ. Certain embodiments of a pharmaceutical dosage form according to the present invention may also keep open a hollow organ, however besides the object of keeping open a hollow organ their object is at least to improve the local application of a drug, particularly an active pharmaceutical ingredient. Some of the other embodiments of a pharmaceutical dosage form according to the present invention have the object to improve the local application of a drug, in particular an active pharmaceutical ingredient, and to let a hollow organ close, in particular even during the application of the dosage form. Particularly, this may be an achieved by a pharmaceutical dosage form comprising a string member or a sheet like preparation that is, in particular in an expanded form, string shaped, cord shaped, strip shaped or tube shaped. In particular, this is especially advantageous for the treatment of the esophagus.

In certain embodiments of the pharmaceutical dosage form according to the present invention the string-like or strip-like preparation is in a solid-state, in particular while it is in its compact form and/or immediately after its release. This may beneficially enhance, enable or facilitate some of the above mentioned advantages. In particular, this may enhance the storability, when it is in a solid state prior the release. In particular, this may enhance and/or enable a targeted and/or sustained release of the active pharmaceutical ingredient, when it is in a solid state after its release. Additionally or alternatively, in certain embodiments of the pharmaceutical dosage form according to the present invention the string-like or strip-like preparation is adapted to dissolve, e.g. bio-degenerate, immediately, after a delay, in a time controlled manner or upon a stimulus after its release. This may beneficially enhance, enable or facilitate some of the above mentioned advantages. In particular, this can improve the user convenience, because the sheet like preparation does not need to be removed.

All embodiments of the pharmaceutical dosage form according to the present invention show the advantage that a pharmaceutical dosage form is provided in which the bioavailability of the active pharmaceutical ingredients contained in the administered dosage form is improved or in which, in particular additionally or alternatively, the local effect of the active pharmaceutical ingredient is improved. Additionally, by means of a pharmaceutical dosage form according to the present invention a dosage form is provided in which the release of the active pharmaceutical ingredient at its predetermined site of action is improved. Further advantageous of the pharmaceutical dosage form according to the present invention are:

Equal effect possible at lower dosages
Reduction of side effects due to a low dosage
Faster onset of effect by direct contact with the application site.

The invention is also related to a method of producing the pharmaceutical dosage form according to the invention, including the steps:

Providing a capsule device including an opening;
Placing a preparation having an elongated shape and comprising the active pharmaceutical ingredient, in a compact condition of the preparation, inside a hollow space of the capsule device and let an end portion of the preparation extend through the opening, the opening and the preparation being configured such that, when the preparation is pulled out from the opening, a spacing (S1; S2) is provided in the opening cross section (CS) of the opening (5) between the preparation (2) and a surface (5a) of the capsule device defining the opening (5).

The step of providing the capsule device may also comprise the steps of providing at least a first part, in particular a first half, of a capsule device and providing at least a second part, in particular a second half, of a capsule device. The step of placing the preparation is performed, preferably, by placing the preparation in the first part or first half of the capsule device, preferably followed by letting the end portion of the preparation extend through the opening, and by connecting the second part, or second half, to the first part or first half of the capsule device. The first part or first half or second part or second half, respectively, may be a tube element or capped tube element or may be a cylinder segment, in particular a half-cylindrical element.

The invention is also related to a method of producing a capsule device for a pharmaceutical dosage form according to the invention, including the steps:

providing a material for forming a capsule device;
generating an opening, in particular a slit, in a material of the capsule device;
forming the capsule device.

The step of forming the capsule device using the material for forming a capsule device may be applied after the step of generating the opening in the material of the capsule device. The step of forming the capsule device using the material for forming a capsule device may also be applied before the step of generating the opening in the material of the capsule device.

The opening may be generated by using a workpiece having a suitable shape.

The material for forming a capsule device may be a workpiece. The workpiece may have, in a respectively preferred embodiment, the shape of a foil, a hollow cylinder, a capsule or a halve of a capsule.

The capsule device is preferably formed such that—when a preparation having an elongated shape and comprising the active pharmaceutical ingredient, is inserted—in a compact condition of the preparation—inside a hollow space of the capsule device and an end portion of the preparation is extended through the opening, and the preparation being capable to be pulled out from the opening—a spacing (S1; S2) is provided in the opening cross section (CS) of the opening (5) between the preparation (2) and a surface (5a) of the capsule device defining the opening (5). The capsule device is preferably formed to be swallowable by a patient.

The step of forming the opening may comprise at least one of the following features:
- using a planar milling tool, e.g. a planar saw blade, or by another tool resulting in a plate-shaped cutting volume, e.g. a cylindrical milling head performing a lateral motion;
- using a laterally moved waterjet in process of abrasive waterjet cutting;
- using a laser to cut or to ablate material from the capsule material;
- punching through the capsule material to create a hole hole via shearing;
- injection molding of a suitable material, e.g. plastic, for forming the capsule device.

The step of forming the capsule device may comprise the step of applying a dip molding process, for producing two halves of a capsule which are joined to form the capsule, as for example, described in EP0102832A2. The step of forming the capsule device may comprise the step of applying a process of additive manufacturing for forming the capsule from a suitable material, in particular a 3D-printing process for forming the capsule from a suitable material. The step of forming the capsule device may comprise the step of injection molding a capsule from a suitable material.

Further preferred embodiments of the method of producing the pharmaceutical dosage form according to the invention and further preferred embodiments of the method of producing a capsule device for a pharmaceutical dosage form according to the invention may be taken from the description of the pharmaceutical dosage form according to the invention and its embodiments, as well as from the description of the embodiments according to the figures.

Exemplary embodiments of the present invention will be described in greater detail below with reference to the accompanying drawings and samples, from which further features, advantages, and embodiments can be learned.

FIG. 1c shows a detail of the area marked by "X" in FIG. 1a.

FIG. 1d shows an alternative configuration of the area marked by "X" in FIG. 1a.

FIG. 2e shows a front view of the capsule device in FIG. 2a.

FIG. 3a shows an isometric oblique view of a dosage form according to a third embodiment of the invention.

FIG. 3b shows the dosage form of FIG. 3a, consisting of two parts of the capsule device and the strip-shaped preparation, before assembly of the capsule device.

FIG. 3c shows a front view of the dosage form in FIG. 3a.

FIG. 3d shows a front view of the arrangement in FIG. 3b.

FIG. 3e shows an oblique bottom view of the dosage form in FIG. 3a.

FIG. 3f shows a side view of the arrangement form in FIG. 3b.

FIG. 5a shows an oblique isometric side view of a capsule part of a capsule device being part of a dosage form according to a fourth embodiment of the invention.

FIG. 5b shows an oblique isometric side view of a capsule part of a capsule device being part of a dosage form according to a fifth embodiment of the invention.

FIG. 5c shows an oblique isometric side view of a capsule part of a capsule device being part of a dosage form according to a sixth embodiment of the invention.

FIG. 6a shows the capsule part of FIG. 5a, in a top view.

FIG. 6b shows the capsule part of FIG. 5b, in a top view.

FIG. 6c shows the capsule part of FIG. 5c, in a top view.

FIG. 7a shows, in a side view, a schematic cross section of the capsule part of FIG. 5a and a strip-like preparation, in its compact condition, being placed inside the capsule part and extending through the opening of the capsule device.

FIG. 7b shows, in a side view, a schematic cross section of the capsule part of FIG. 5b and a strip-like preparation, in its compact condition, being placed inside the capsule part and extending through the opening of the capsule device.

FIG. 7c shows, in a side view, a schematic cross section of the capsule part of FIG. 5c and a strip-like preparation, in its compact condition, being placed inside the capsule part and extending through the opening of the capsule device.

FIG. 7d shows a modified version of the embodiment of FIG. 7c, wherein the width of the slit-like opening is larger than in FIG. 7c.

FIG. 7e is a schematic side view of the embodiment of a capsule part in FIG. 5b, describing the position of the opening being a planar curved slit.

FIG. 9b shows an illustration explaining a second step of the procedure starting with FIG. 9a.

FIG. 9c shows an illustration explaining a third step of the procedure starting with FIG. 9a.

FIG. 9d shows an illustration explaining a fourth step of the procedure starting with FIG. 9a.

FIG. 11 shows a flow chart of a testing and selection protocol used to test a preparation in the form of a wafer suitable for the present invention.

Figure 1A:
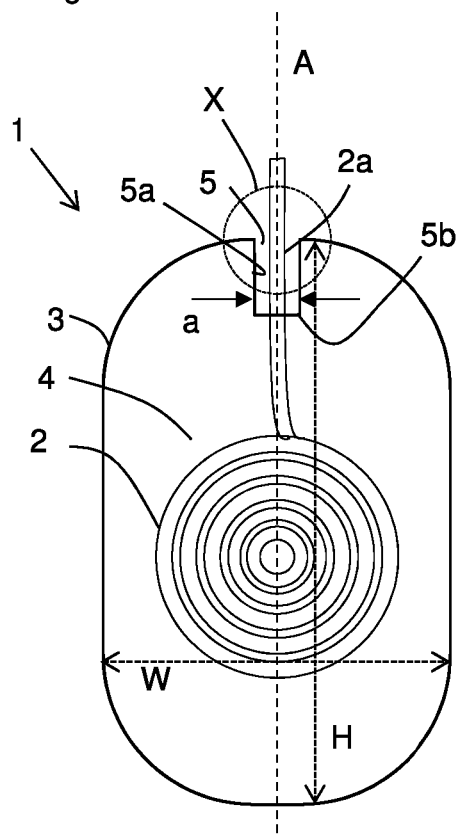
FIG. 1a shows a schematic side view of a dosage form according to a first embodiment of the invention.
Figure 4A:
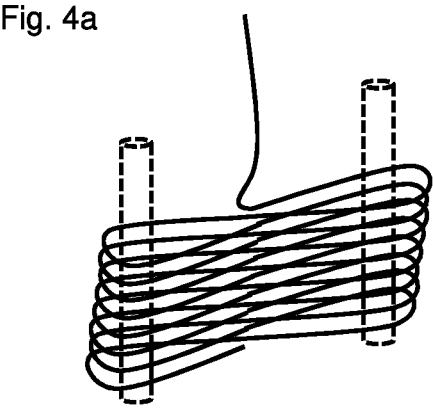
FIG. 4a shows a perspective side view of a string-like preparation, in its compact condition, which is suitable for use in a dosage form according to the invention.
Figure 4B:
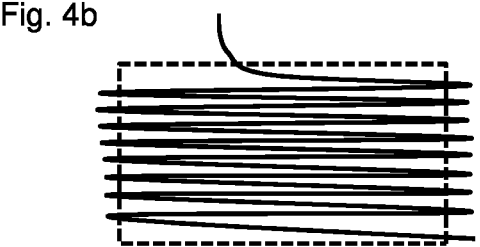
FIG. 4b shows a side view of another string-like preparation, in its compact condition, which is suitable for use in a dosage form according to the invention.
Figure 4C:
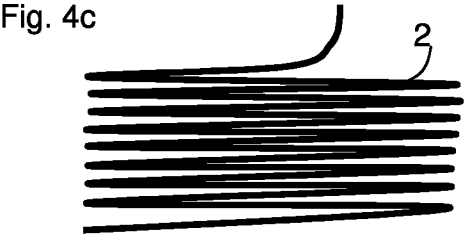
FIG. 4c shows a side view of a strip-like preparation, in its compact condition, which is suitable for use in a dosage form according to the invention.
Figure 4D:
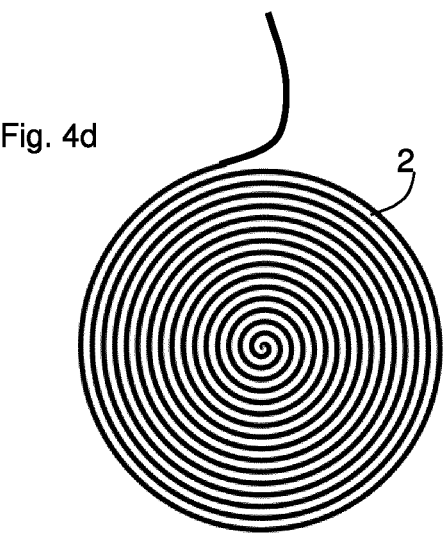
FIG. 4d shows a side view of another strip-like preparation, in its compact condition, which is suitable for use in a dosage form according to the invention.
Figure 4E:
FIG. 4e shows a side view of the string-like preparation of FIG. 4a or FIG. 4b, in its expanded condition.
Figure 4F:
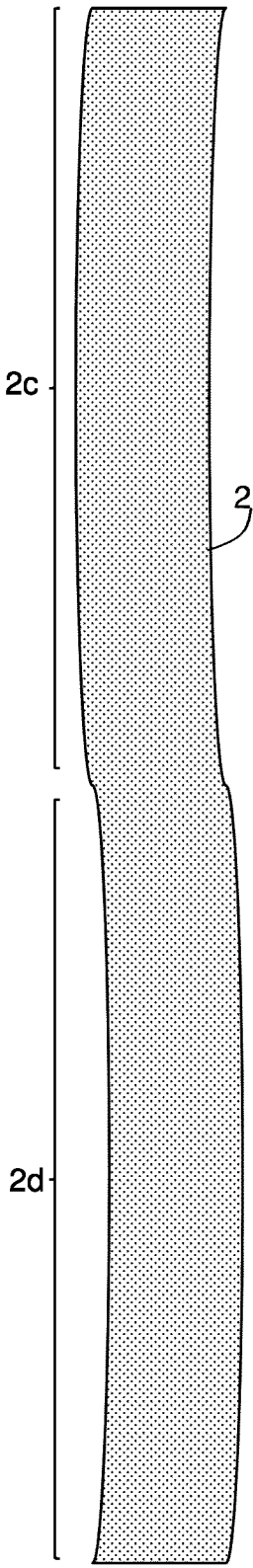
FIG. 4f shows a side view of the strip-like preparation of FIG. 4c or FIG. 4d, in its expanded condition.

FIG. 1a shows the pharmaceutical dosage form 1 for the application to a mucous membrane, in particular to a buccal, gastro-intestinal, rectal or vaginal mucous membrane, comprising a preparation 2 having an elongated shape and comprising the active pharmaceutical ingredient. The preparation 2 is shown in a compact condition: assuming that the preparation has a strip-like shape, FIG. 1a shows a side view of the strip-like preparation being wound as a spiral around a virtual axis, which is perpendicular to the drawing sheet. In an expanded condition, when the preparation is pulled out from the slit-like opening 5 of the capsule 3, the strip-like preparation will have an elongated shape of a substantially straight strip, as shown in FIG. 4f.

The capsule device 3 has the shape of a capsule and comprises a hollow space 4, which accommodates the preparation 2 being in the compact condition. The capsule consists of a thin wall having a thickness of about 50 μm to 200 μm, made from a biodegradable or non-biodegradable material.

The capsule device has an opening 5, which is a planar curved slit being centered with the central length axis A of the capsule 3. Such a slit may be produced by milling out the capsule material using a plate-shaped milling tool, for example a plate shaped saw blade. The width a of the planar curved slit is defined by measuring the distance of opposing surfaces 5a of the capsule wall in a direction perpendicular to the length axis A. The distance 'a' may be a constant value between 200 μm and 600 μm, for example. The thickness t of the preparation may be a constant value between 20 μm and 150 μm, for example.

Figure 1B:
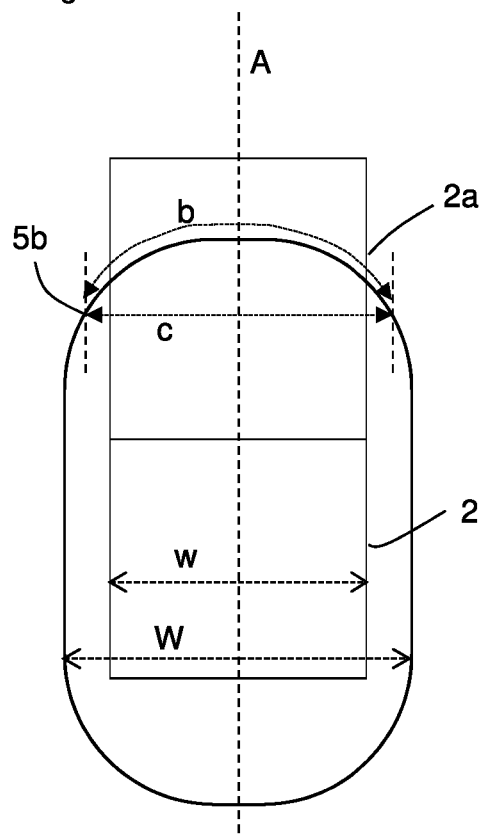
FIG. 1b shows the dosage form of FIG. 1a, rotated by 90° around the central length axis A.

As shown FIG. 1b, where the dosage form is turned around the axis A by 90°, the length of an outer edge of a surface 5a is denoted as 'b'. Since the upper cap of the capsule 3 carrying the slit, has a convex shape, the distance b is larger than the distance 'c', which denotes the direct connection between the two opposing end points 5b of a single outer edge of a surface 5a. The rectangular area (not directly shown), which is defined by the four edge points 5b of the slit-like opening and which has a size of a*c, is also referred to as passage cross section, because it limits the area which is available for the strip 2 when passing through the slit 5, the strip 2 having a rectangular cross section small enough to pass by the surfaces 5a in a distance (=spacing).

Regarding the outer dimensions of a capsule device, for example, the height H of the capsule 3 may be 8 mm, the width W of the capsule may be 4 mm. However, other dimensions of a capsule device are generally possible taking into account the desired administration site of a patient.

A first end 2a of the preparation 2 extends, in the compact condition of the preparation, through the opening 5 for allowing grabbing and pulling out the preparation from the hollow space into the surrounding area of the capsule device, thereby transferring the preparation 2 from the compact condition to the expanded condition. Pulling out the preparation, i.e. the pull-out movement P (cf. FIG. 1c), may be the result of fixating and end 2a of the preparation 2 and pulling the capsule device in a direction M opposite to P. This is the case for example, by using the process of administering the capsule device by swallowing the same, and fixating the end 2a of the preparation at the teeth of a patient (cf. FIG. 9a to 9d).

The first end 2a may have an end portion (cf. FIG. 1d), which has a shape different from the strip 2. For example, the end portion may form a sealing part suitable to be arranged at the opening 5 for sealing the opening 5, before the end portion is pulled out from the opening.

The slit-like opening 5 and the strip-like preparation 2 are dimensioned such that, when the preparation is pulled out from the opening, a spacing (S1; S2; cf. FIG. 1c) is provided measured in the opening cross section CS of the opening 5 between the preparation 2 and a surface 5a of the capsule device defining the opening 5. Here, the central length axis A of the capsule runs perpendicular to the opening cross section CS.

Figure 1C:
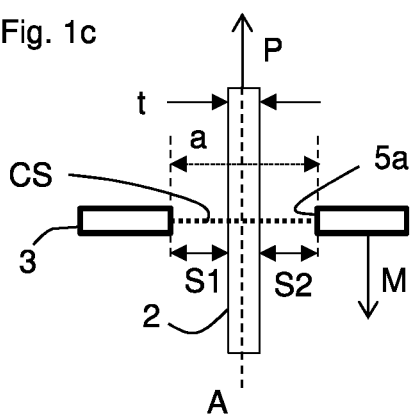

As shown in FIG. 1c, the thickness t of the strip 2 is remarkably smaller than the width a of the planar curved slit 5. For example, the thickness t may be a constant value between 20 μm and 150 μm. The spacing S=S1=S2 is measured by positioning the preparation 2 in the center of the opening 5 and in a centered-and-aligned position of the strip surfaces being in parallel to and facing the surfaces 5a of the capsule. The spacing S is present and may be —in average-substantially constant while the preparation 2 is pulled out from the opening, which means, substantially along the whole length of the elongated preparation (cf. FIGS. 4e, 4f). However, the scope of the invention also may cover embodiments of dosage forms, where the spacing between the preparation and the surfaces 5a, which define the opening, varies —due to a varying thickness t of the preparation 2—, or where the spacing is partly interrupted —due to a portion-wise variation of dimensions a and t, including the portion-wise dimensioning of a=t.

In cases, where the preparation has a string-like shape, the dimensions may be measured in analogy, and in case of irregularly shaped preparation, the dimensions may be determined by averaging.

Figure 1D:
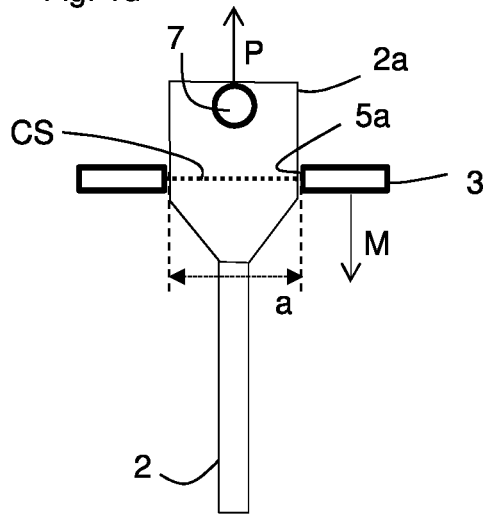
Figure 2A:
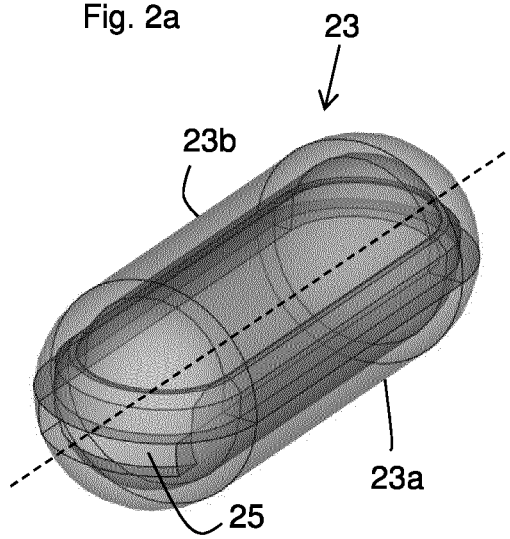
FIG. 2a shows an isometric oblique view of a capsule device being part of a dosage form according to a second embodiment of the invention.
Figure 2B:
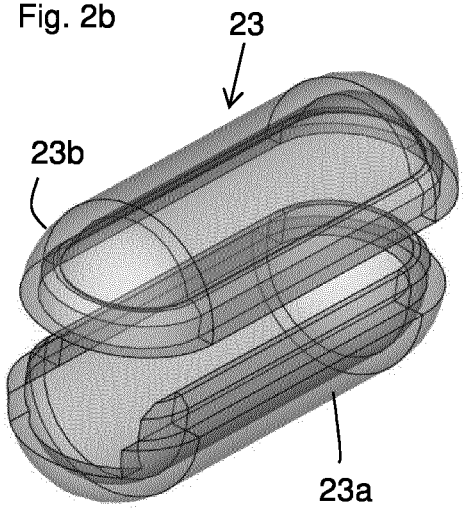
FIG. 2b shows the capsule device of FIG. 2a, consisting of two parts, before assembly of the capsule device.
Figure 2C:
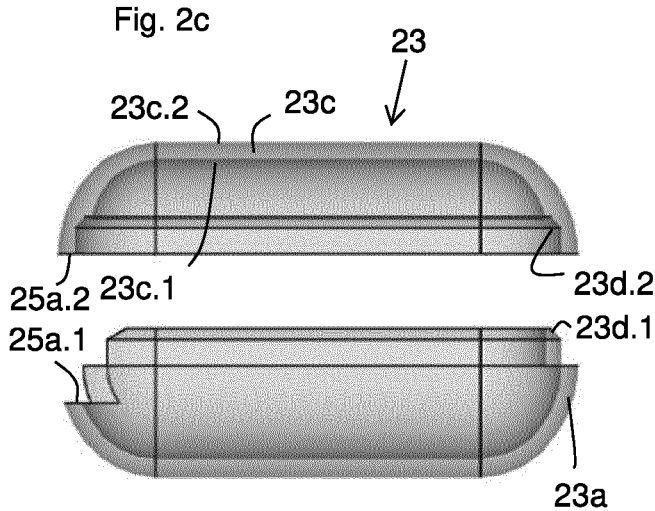
FIG. 2c shows a side view of the arrangement in FIG. 2b.
Figure 2D:
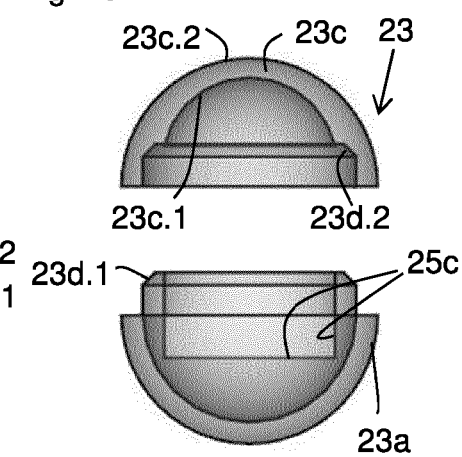
FIG. 2d shows a front view of the arrangement in FIG. 2b.
Figure 2E:
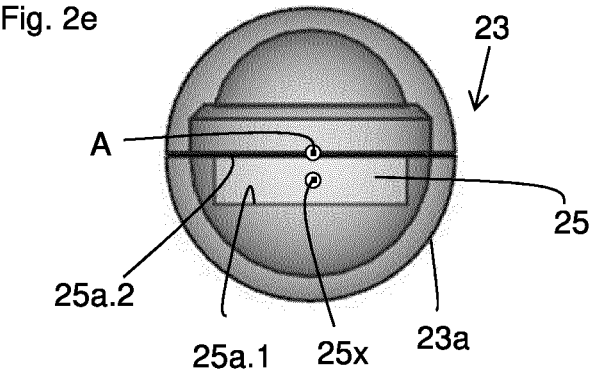

As shown in FIG. 1d, the first end 2a may have an end portion forming an enlarged part, which may be configured for avoiding that the preparation is lost inside the capsule 3, which would make it different for a patient or applicant to recover the end 2a for pulling out the strip and applying the dosage form in the predetermined way. The end portion 2a may also be configured to be arranged at the opening 5 for sealing the opening 5, before the end portion is pulled out from the opening. A portion 7 may be provided at the end part, being configured to connect a line to the end part, which may be used by a patient or applicant to grab the preparation or manipulate the preparation. The line may be fixated at the teeth of a patient, instead of the end 2a being directly fixated to the patient, in case of the oral administration of the dosage form shown in FIG. 9a to 9d.

FIG. 2a to 2e show different arrangements of a capsule device 23, and the two half-cylinder elements 23a and 23b forming the capsule device. The manufacture of the two half-cylinder elements may use a type of molding process. The setup of the capsule 23 is different compared with the capsules in FIG. 5a to 5c, which capsules may be traditionally produced by a Colton process, including joining of two tube elements, followed by a step of providing the capsules with an opening. The lower part contains a cuboid recess 25c on one of its rounded end faces. Such a configuration allows to easily assembly the dosage form by arranging the lower part 23a of the capsule 23 horizontally with the hollow space facing upwards, and by placing the compacted preparation inside the hollow space of the lower part 23a and then simply dropping the end portion 2a of a preparation onto the surface 25a.1, which defines the opening 25, followed by a step of placing the upper half part 23b onto the lower half part 23a. The parts may be connected by adhesion, force fit and/or using an adhesive. Positioning of the two half parts 23a, 23b is such that the surfaces 25a.1 and 25a.2 are aligned opposite to each other, thereby defining the opening 25. The opening 25 is arranged offset form the length axis A, which means that the axis A does not cross the center point 25x of the opening 25. The surface 25a.2 is defined by an outer surface of the halve part 23b. The lower half 23a of the capsule device has a (male) connector part 23d.1, here configured to be a protrusion 23d.1 of the connecting side of the halve part 23a, which runs circumferentially around the inner space of the capsule device and thereby forms a ring-shaped protrusion. The upper half has a corresponding connector part 23d.2, here configured to be a recess 23d.2 of the connecting side of the half part 23b, which runs circumferentially around the inner space of the capsule device and thereby forms a ring-shaped recess, configured to receive the protrusion 23d.1 by a form-fit connection, which secures the precise relative positioning of the two half-cylinder elements 23a, 23b.

Each half-cylinder element 23a, 23b of the capsule device 23 in FIGS. 2a to 2e is made from one wall 23c, which has an inner side 23c.1 and an outer side 23c.2, which sides run in parallel to each other. The resulting hollow space of the capsule device 23 is basically shaped similar to the outer contour of the capsule 23, which means the hollow space is capsule-shaped, including a hollow-cylindrical part, which is capped by a hollo-semi-sphere portion at each end of the cylinder, wherein one of the (hollow) cap parts is connected to the opening 25. Any edges of the opening 25 may be alternatively trimmed to avoid sharp edges.

FIGS. 3a to 3f show the arrangement of a dosage form 31, which has a capsule device 33. The capsule device 33 has the same features as the capsule device 23 shown in FIG. 2a to 2e, except from the shaping of the hollow space, or the inner side of the capsule walls, respectively. Moreover, the strip-like preparation 32 is shown here, which is placed in the hollow space of the capsule device 33 and extends through the opening 35. The same preparation 32 may be used to form a dosage form using the capsule device 23 of FIGS. 2a to 2e.

The inner sides 33c.1, 33c.3 of the capsule walls 33c are shaped to provide a substantially cuboid shaped hollow space. Each side acts as a guiding member 33c.1, 33c.3. Such a cuboid shaped hollow space offers the functionality of a guiding compartment for guiding the position of the winding of the strip-like preparation 2, which may be advantageous in particular during the process of unwinding the compacted preparation 2 during pulling out of the preparation. It was found that the cuboid hollow space, which provides a kind of form-fit casing of the preparation 2 (being in the shape/condition of a cylindrical coil), provides a guiding structure, which stabilizes the preparation against a rotation around the central length axis A. Thereby, twisting of the preparation around the axis A is avoided and the unwinding process becomes more reliable, in particular in cases where the preparation is rather deformable.

FIGS. 5a to 5c, respectively, show a capsule part 43a, which has the shape of a cylindrical part being capped by a semi-sphere shaped part, which carries a slit-like opening 45.1, 45.2, 45.3, respectively. Such capsule parts may be produced by the known Colton method, and a corresponding cylindrical counter part (not shown) may be used to close the capsule part 43a—after placing a compacted preparation inside the hollow space of the capsule part 43a—and to thereby form a dosage form according to the invention. The slit-like opening 45.1, 45.2, 45.3 may be provided by milling out a plate shaped recess form the capsule material using a plate shaped milling tool, e.g. a saw blade or any tools having a comparable effect.

FIGS. 7a to 7c correspond to the embodiments of capsule parts 43a shown in FIGS. 5a to 5c and 6a to 6c, respectively, wherein the positioning of the slit like opening is varied. In each case, the position of the opening 45.1, 45.2, 45.3, 45.3' is offset from a length axis A of the capsule part 43. The opening 45.3 is equal to the opening 45.3', but the width a.2 of the opening 45.3' is larger than the width a.1 of the opening 45.3, by about 50%, such that a.2=1.5*a.1. The drawings of FIG. 7a to 7d are copied in the diagram of FIG. 8.

The slit-like opening 45.2 is arranged such that the normal N of the main plane of the planar curved slit 45.2 and the central axis A of the capsule part 43a include an angle α=45° (cf. FIG. 7e). For the slit-like opening 45.1, where the slit-like opening is offset from the central axis A of the capsule part, the angle α is Null. In another preferred configuration of the slit-like opening 45.3, 45.3', the angle α is 90°, respectively. The slit-like openings 45.1, 45.2, 45.3, 45.3' are, respectively, arranged such that a main plane running through the opening is in parallel to an axis B, which is perpendicular to the central axis A of the capsule device (cf. FIG. 7e). Such a configuration matches to a winding of a strip-like preparation, which is wound around a winding axis being parallel to axis B, and facilitates the unwinding process.

Figure 8:
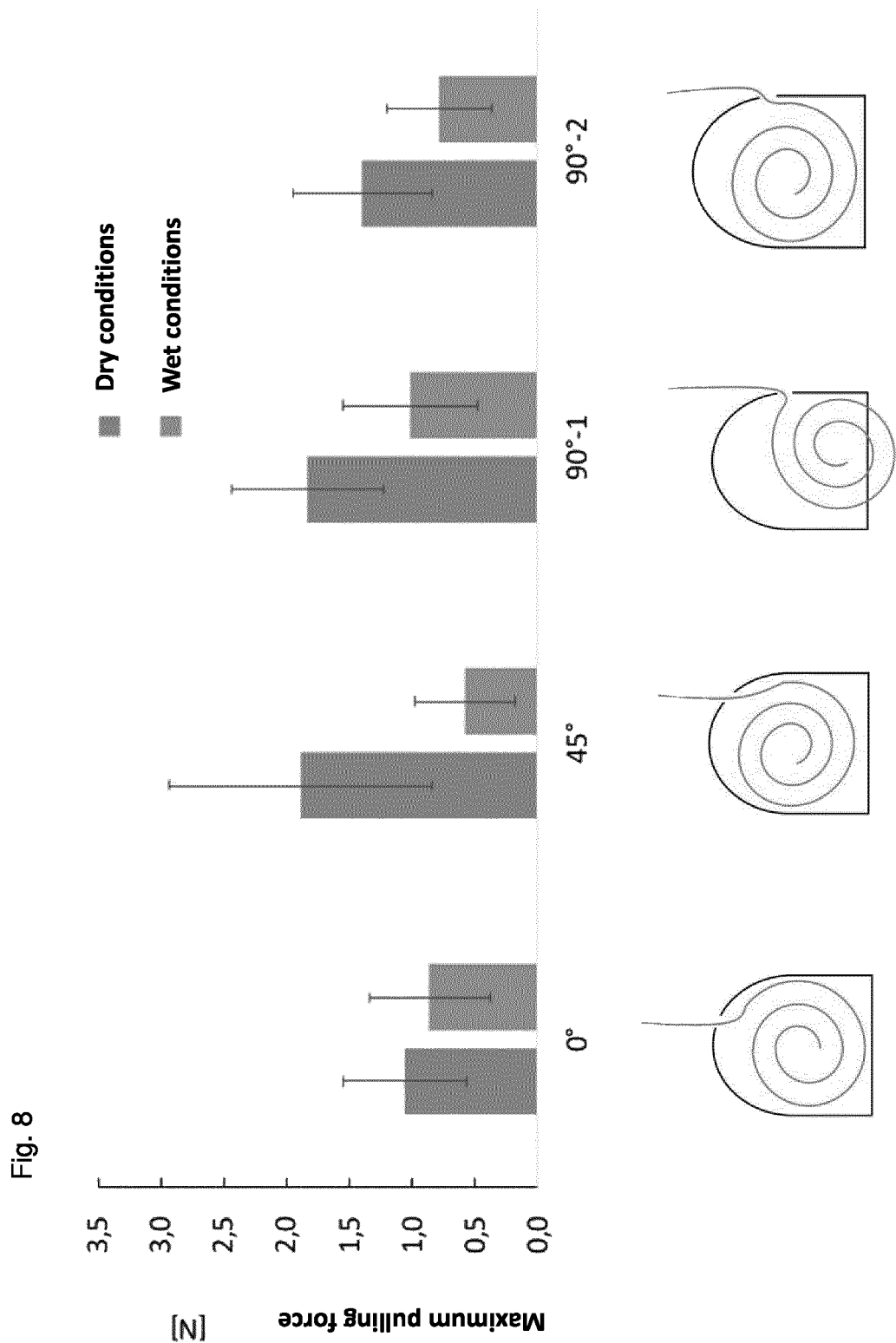
FIG. 8 shows a diagram with results of pulling force experiments performed with dosage forms corresponding to the embodiments shown in FIGS. 7a to 7d, under dry and wet conditions, respectively.

The diagram of FIG. 8 shows that the maximum pulling force, which occurs when pulling out a strip-shaped preparation 2 from a dosage form having a capsule part 43 a and one of the different types of openings 45.1, 45.2, 45.3, 45.3', differs depending of the type of opening and depending of the choice of a dry or wet condition. For performing the experiments, a standard setup for measuring tensional forces was used. The dosage form was arranged and fixated in a vertical position, with the central length axis of the capsule part 43a being vertically arranged. The end portion of the strip-like preparation 2, which in each case extended through the opening, was connected to a force sensor. The force sensor with the end portion of the preparation was then vertically raised by a constant velocity of somewhere between 0.01 to 0.05, e.g. 0.02 m/s and the maximum force was determined by continuously monitoring the occurring forces. In case of dry conditions, the preparations, which were stored under room temperature 21° C. and standard humidity, were directly transferred to the force measurement apparatus and measured. In case of the wet conditions, the dosage forms were rinsed for 10 seconds with distilled water and then transferred to the force measurement apparatus and measured. Surprisingly, the maximum tension force was generally lower in the case of wet conditions compared to dry conditions, and no rupturing of the preparation was observed during the experiments, either under wet or dry conditions. Enlarging the width of the slit (compare the results for openings 45.3 and 45.3') results in a lower maximum pulling force.

Figure 10:
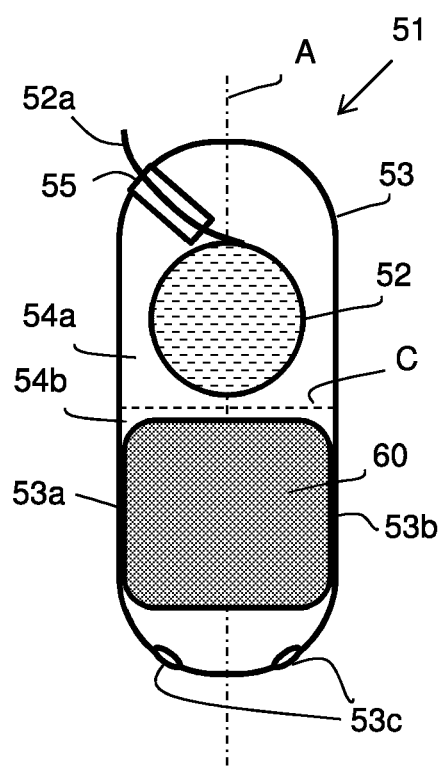
FIG. 10 shows a schematic side view of a dosage form according to a further embodiment of the invention.

FIG. 10 shows a pharmaceutical dosage form 51 for the application to a mucous membrane, in particular to an esophageal membrane comprising a preparation 52 having an elongated shape with an end portion 52*a* and comprising an active pharmaceutical ingredient, the at least one preparation being capable to be arranged in a compact condition and in an expanded condition and a capsule device 53 comprising a hollow space 54*a*, 54*b* for accommodating the preparation 52 being in the compact condition. More specifically, the preparation is located inside the upper half 54*a* of the hollow space, the "upper half" meaning that said half is oriented towards the upstream direction when the dosage form is swallowed with a stream of water by a patient. Inside the lower half 54*b* of the hollow space, a sinker element is clamped between opposing sides 53*a*, 53*b* of the capsule's inner side. The sinker element 60 is a basically cylindrical part and coaxially arranged with the capsule device along its axis A. The sinker device 60 occupies the larger part of the lower half 54*b* of the hollow space. The "lower half" meaning that said half is oriented towards the downstream direction when the dosage form is swallowed with a stream of water by a patient. The upper half and the lower half are illustrated also by the virtual line C, which divides the hollow space in the two substantially equally dimensioned volumes 54*a*, 54*b*. The presence of the sinker element 60 avoids that the lower half 54*b* of the hollow space is filled with air. The sinker element is made of a glucose, for example, having a density of about 1.5 g/cm$^3$, thereby being heavier than water. The weight element 60 will improve the efficiency of the expansion of the compacted strip-like preparation 52 by a gravity driven displacement in downstream direction, when the dosage form is administered by a patient in the presence of a stream of water. The placement of the sinker element 60 in the lower half 54*b* of the capsule's hollow space will assist to align the capsule with the direction of stream, which may substantially be the direction of gravity.

The sinker element 60 and the dosage form 51, respectively, were produced by a method according to the invention, using a process of tablet pressing a graular material mixture, which exemplarily comprised the following excipients: Croscarmellose-Na 0.25; Calcium hydrogen phosphate anhydrate 97.75; Magnesium Stearate 1.5; Highly dispersed silica 0.5, all numbers in mol %.

The physical properties of the sinker element 60 being a pressed tablet, which fits inside the lower half of the capsule, having a diameter of 7.0 mm, are as follows: Density: approx. 1.65 g/cm$^3$; Mass: 366 mg±5%; Height: 5.3-5.7 mm; Diameter: 6.95 mm.

The overall density of the dosage for 51 without the sinker element 60 was 0.4 g/cm$^3$, the overall density of the dosage for 51 with the sinker element 60 was 1.05 g/cm$^3$.

The sinker element, alternatively, may also be porous by containing open pores allowing water entering the pores. The porous material may be any absorbent material. In this case, the water entering the pores and displacing the air will contribute to a negative buoyancy provided by the sinker device.

The capsule device has an opening 55 and a first end 52*a* of the preparation extending, in the compact condition, through the opening 55 for allowing pulling out the preparation from the hollow space into the surrounding area of the capsule device thereby transferring the preparation from the compact condition to the expanded condition. During administration, the end 52*a* of the preparation may be fixed to the teeth of the patient. Also here, the opening 55 and the preparation 52 are dimensioned such that, when the preparation is pulled out from the opening 55, a spacing is provided in an opening cross section of the opening between the preparation and a surface of the capsule device defining the opening. The spacing and, in this embodiment, additionally the optional pores 53*c* extending through the wall of the capsule device, allow water to enter the hollow space, while air leaves the hollow space. In this case, the water entering the pores and the opening, thereby displacing the air, contributes to a negative buoyancy provided by the sinker device.

The dosage form according to the invention is further elucidated by the following examples.

Example 1

The single-layered or multi-layered preparation according to the present invention preferably has a paper-like form.

The preparation according to the present invention dissolves preferably within 1 h, more preferably within 30 min, most preferably within 15 min and particularly most preferably within 5 min after contact with the site of action, in particular the mucous membrane.

They essentially comprise a mucoadhesive, active substance containing layer, which preferably comprises: mucoadhesive polymers such as cellulose derivatives, starch and starch derivatives, polyvinyl alcohol, polyethylene oxide, polyethylene, polypropylene, polyacrylic acid, and polyacryl derivatives, polyvinylpyrrolidone, povidone, copovidone, sodium alginate, gelatin, xanthan gum, guar gum, carrageenan, pectins, dextrans, lectins, chitosan, pullulan, and mixtures thereof, plasticizers such as polyethylene glycol, glycerol, sorbitol, and mixtures thereof, and solvents such as water, ethanol, methanol, acetone, organic solvents, and mixtures thereof. Furthermore, additives such as colorants, fragrances, flavoring agents, preservatives, antioxidants, penetration enhancers, solubilizers, disintegration accelerators, lubricants, and mixtures thereof may be contained.

In particular, substances out of the following groups are suitable as active pharmaceutical ingredients: drugs acting on the skeleton and the muscles, drugs acting on the nervous system, hormones and drugs acting on the hormonal system, gynecological acting drugs, drugs acting on the cardiovascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides.

Development and Testing

In order to develop and test a preparation in the form of a wafer suitable for the present invention, testing methods based on the test and selection protocol 1 shown in FIG. 11 have been conducted.

In this way, preparations are obtained that meet the requirements which arise, in particular, for a usage in connection with the dosage form.

In particular, the wafers according to the present invention are distinguished over previously known wafers by the fact that they do not dissolve at just a slight contact with fluid already and that they have a relatively high stretchiness and fracture resistance.

Especially for a vaginal, rectal or intestinal mucous membrane, a tensile strength of less than 3.5 MPa may be beneficial to increase the safety, the user convenience and/or to enable a close but flexible fitting of the sheet like preparation with the respective mucosa.

Especially for an esophageal mucous membrane and/or for the application to the esophagus, a tensile strength of more than 15 MPa may be beneficial, particularly for avoiding a rupture of the sheet like preparation during its application, especially during swallowing the dosage form.

Example 2—Single-Layered Preparation

Single-layered preparations, in particular wafers, that are suitable for the usage according to the invention, may, in particular, comprise the following formulations:

| | |
|---|---|
| A | 10% PVA |
| | 20% PEG 400 |
| | 5% HPMC |
| | x % active pharmaceutical ingredient |
| | ad 100 % demineralized water |
| B | 5% PVA |
| | 15% Kollicoat ® IR |
| | x % active pharmaceutical ingredient |
| | ad 100 % demineralized water |
| | or |

-continued

| | |
|---|---|
| C | 5% PVA |
| | 15% Kollicoat ® IR |
| | 8% Glycerol 85 % |
| | x % active pharmaceutical ingredient |
| | ad 100 % demineralized water |

Example 3—Two-Layered Preparation

Two-layered preparations, in particular wafers, according to the present invention comprise a mucoadhesive layer containing an active substance and a water-impermeable layer, which is called a backing layer. The mucoadhesive layer containing an active substance is preferably composed of mucoadhesive polymers as cellulose derivates, starch and starch derivates, polyvinyl alcohol, polyethylene oxide, polyethylene, polypropylene, polyacrylic acid and polyacrylate derivates, polyvinylpyrollidone, Povidone, Copovidone, sodium alginate, gelatin, xanthan gum, guar gum, Carrageenan, pectins, dextrans, lectins, Chitosan, Pullulan an mixtures thereof, plasticizers such as polyethylene glycol, glycerol, sorbitol and mixtures thereof, and the solvent such as water, ethanol, methanol, acetone, organic solvents and mixtures thereof. Furthermore, additives such as colorants, fragrances, flavoring agents, preservatives, antioxidants, penetration enhancers, solubilizers, disintegration accelerators, lubricants, and mixtures thereof may be contained. Substances of the following group are suitable as active pharmaceutical ingredients: Drugs acting on the skeleton and on the muscles, drugs acting on the nervous system, hormones and drugs acting on the hormonal system, gynecological acting drugs, drugs acting on the cardio-vascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives and parasizides.

The backing layer preferably comprises an ethyl cellulose layer of varying thickness, wherein ethyl cellulose of different viscosities may be used. Furthermore, it is possible to incorporate further additives such as colorants, fragrances, flavoring agents, preservatives, antioxidants, solubilizers, pore formers, lubricants, and mixtures thereof.

Table 1 which follows shows various exemplary compositions of layers of a two-layered wafer 3 according to the present invention.

TABLE 1

| Adhesive layer containing an active substance | | | | | |
|---|---|---|---|---|---|
| PVA | 10% | 10% | 10% | 10% | 10% |
| PEG 400 | 20% | 20% | 20% | 20% | 20% |
| HPMC | 5% | 5% | 5% | 5% | 5% |
| Active pharmaceutical ingredients | x % | x % | x % | x % | x % |
| Water | ad 100% | ad 100% | ad 100% | ad 100% | ad 100% |
| Water-impermeable layer (backing layer) | | | | | |
| Ethyl cellulose 10 (4% solution in acetone) | 300 µg EC/cm$^2$ | 400 µg EC/cm$^2$ | 500 µg EC/cm$^2$ | 750 µg EC/cm$^2$ | 5000 µg EC/cm |
| Ethyl cellulose 45 (4% solution in acetone | 300 µg EC/cm$^2$ | 400 µg EC/cm$^2$ | 500 µg EC/cm$^2$ | 750 µg EC/cm$^2$ | 5000 µg EC/cm |

The strip-like, in particular film-shaped, foil-shaped, wafer-shaped preparation 2 comprising the active pharmaceutical ingredient comprises at least one first layer containing the active substance. The layer containing the active substance preferably comprises a polymer, more preferably a film-forming polymer, wherein the polymer fraction in the layer containing the polymer and the active substance is 10 to 90% by weight, preferably 20 to 70% by weight, and more preferred 30 to 60% by weight, and wherein the layer containing the active substance, in particular in a two-layered wafer, is an adhesive layer, and wherein the polymer is a water-dispersible and/or water-decomposable and/or water-disintegrable film-forming polymer.

Furthermore, the strip-like, in particular film-shaped or wafer-shaped preparation 2 comprising the active pharmaceutical ingredient comprises at least one active substance free layer, that does not contain an active pharmaceutical ingredient. In a three-layered wafer 2 the wafer 2 comprises a further active substance-free layer that also does not contain an active pharmaceutical ingredient. Such a first active substance free layer and/or such a further active substance free layer is preferably a water-insoluble layer, e.g. made of or comprising ethyl cellulose. An active substance free layer and/or a further active substance free layer may be formed as an adhesive layer, in particular in a two-layered wafer 2, wherein the layer consists of or comprises e.g. hydroxypropyl methylcellulose. In a multi-layered, in particular three-layered wafer 2 layer containing the active substance is preferably arranged between two active substance free layers,., wherein a layer containing the active substance may be arranged between a first active substance free layer and a further active substance free layer and wherein preferably the first active substance free layer is a water-insoluble layer, which more preferably comprises ethyl cellulose, and wherein the at least one further active substance-free layer 9d is an adhesive layer, which more preferably comprises hydroxypropyl methylcellulose.

Example 4—Three-Layered Preparation

Three-layered preparations, in particular wafers, according to the present invention preferably comprise a mucoadhesive layer containing an active substance, a water-impermeable layer, which is called a backing layer, and an adhesive protective layer. The mucoadhesive layer containing the active substance may be composed of mucoadhesive polymers such as cellulose derivatives, starch and starch derivatives, polyvinyl alcohol, polyethylene oxide, polyethylene, polypropylene, polyacrylic acid, and polyacryl derivatives, polyvinylpyrrolidone, povidone, copovidone, sodium alginate, gelatin, xanthan gum, guar gum, carrageenan, pectins, dextrans, lectins, chitosan, pullulan, and mixtures thereof, plasticizers such as polyethylene glycol, glycerol, sorbitol, and mixtures thereof, and solvents such as water, ethanol, methanol, acetone, organic solvents, and mixtures thereof. Furthermore, additives such as colorants, fragrances, flavoring agents, preservatives, antioxidants, penetration enhancers, solubilizers, disintegration accelerators, lubricants, and mixtures thereof may be contained. In particular, substances out of the following groups are suitable as active pharmaceutical ingredients: drugs acting on the skeleton and the muscles, drugs acting on the nervous system, hormones and drugs acting on the hormonal system, gynecological acting drugs, drugs acting on the cardiovascular system, drugs acting on the respiratory system, drugs acting on the gastrointestinal tract, diuretics, drugs acting on the sensory organs, dermatics, vitamins and micronutrients, peptide based drugs and proteins, analgesics, anti-infectives, and parasizides. The backing layer is made of an ethyl cellulose layer with a varying thickness, wherein ethyl cellulose with various viscosities may be used. Moreover, the incorporation of other additives such as colorants, fragrances, flavoring agents, preservatives, antioxidants, solubilizers, pore formers, lubricants, and mixtures thereof is possible. The adhesive protective layer may vary in its thickness and is made of mucoadhesive polymers such as cellulose derivatives, starch and starch derivatives, polyvinyl alcohol, polyethylene oxide, polyethylene, polypropylene, polyacrylic acid, and polyacryl derivatives, polyvinylpyrrolidone, povidone, copovidone, sodium alginate, gelatin, xanthan gum, guar gum, carrageenan, pectins, dextrans, lectins, chitosan, pullulan, and mixtures thereof, and a solvent such as water, ethanol, methanol, acetone, organic solvents, and mixtures thereof. Furthermore, additives such as colorants, fragrances, flavoring agents, preservatives, antioxidants, penetration enhancers, solubilizers, disintegration accelerators, pore formers, lubricants, and mixtures thereof may be contained.

Table 2 which follows shows various exemplary compositions of layers of such a three-layered wafer 3.

TABLE 2

| | | | | |
|---|---|---|---|---|
| Adhesive protective layer | | | | |
| HPMC (0.5% solution in water) | 50-100 μm layer | 50-100 μm layer | 50-100 μm layer | 50-100 μm layer |
| Mucoadhesive layer containing the active substance | | | | |
| PVA | 10% | 10% | 10% | 10% |
| PEG 400 | 20% | 20% | 20% | 20% |
| HPMC | 5% | 5% | 5% | 5% |
| Active pharmaceutical ingredients | x % | x % | x % | x % |
| Water | ad 100% | ad 100% | ad 100% | ad 100% |
| Water-impermeable layer (backing layer) | | | | |
| Ethyl cellulose 10 (4% solution in acetone) | 300 μg EC/cm$^2$ | 400 μg EC/cm$^2$ | 500 μg EC/cm$^2$ | 750 μg EC/cm$^2$ |
| Ethyl cellulose 45 (4% solution in acetone | 300 μg EC/cm$^2$ | 400 μg EC/cm$^2$ | 500 μg EC/cm$^2$ | 750 μg EC/cm$^2$ |

A sheet-like preparation 3 of a pharmaceutical dosage form 1 according to the present invention may also be formed out of one layer or out of multiple layers, in particular out of two layers.

Example 5

Regarding the Calculation of the Amount of Active Ingredient Per Wafer:

In particular, the amount of active ingredient based on the layer thickness of the wet polymer film can be calculated according to the following formula:

$$m(\text{active pharmaceutical ingredient}) = \frac{m(\text{formulation}) * m\left(\frac{\text{active pharmaceutical ingredient}}{wafer}\right) * 10000}{p(\text{polymer mass}) * A(wafer) * h(\text{doctor blade})}$$

wherein
m mass [g]
p density [g/cm$^3$]
A area [cm$^2$]
h height [μm]

In this context it is important to keep in mind that the height of the doctor blade is not equal to the layer thickness of the wet wafer. Reasons for this are, for example, the shearing of the polymer film while it is spread out, the flowing apart or flowing together of the polymer composition after spreading out, and the formation of thicker regions at the edges of the polymer film. The extent of these processes is, inter alia, dependent on the viscosity of the polymer solution and on the used active pharmaceutical ingredient. Therefore, for each active pharmaceutical ingredient a specific individual fraction may be added to the calculated amount of active ingredient. This additional fraction is
- 35% for sodium fluorescein
- 40% for quinine
- 35% for sodium diclofenac Moreover, one may use a drug specific factor to adjust the calculated amount, wherein, in particular, the drug specific factor is 100%+the additional fraction, and therefore the formula reads:

$$m(\text{active pharmaceutical ingredient}) = \frac{m(\text{formulation}) * m\left(\frac{\text{active pharmaceutical ingredient}}{wafer}\right) * 10000}{p(\text{polymer mass}) * A(wafer) * h(\text{doctor blade})} * \text{drug specific factor}$$

Example 6—Manufacture of Single-Layered Wafers

The manufacture of single-layered wafers is carried out by a solvent casting method, wherein at first all ingredients are dissolved in the solvent, homogenized, and subsequently spread out on a suitable release liner to the desired thickness using a doctor blade. Then, the resulting film is dried under defined conditions and then cut into pieces of suitable size.

In the following, the manufacturing methods for the preparations mentioned in Example 2 above are described in detail:

A At first, polyvinyl alcohol (PVA) is dissolved in demineralized water in a beaker at a temperature of 90° C. and at a stirring speed of 400 rpm. Then, polyethylene glycol 400 (PEG 400) and the medical substance or the medical substance solution, respectively, is added and the solution is homogenized. Finally, hydroxypropyl methylcellulose (HPMC) is added with stirring, homogenized, and the evaporation loss is compensated with demineralized water. The polymer solution is covered and left overnight and centrifuged on the next day at 4400 rpm for 50 min in order to remove air bubbles. Then, the solution is evenly spread out onto the release liner by means of a doctor blade and the polymer film is dried for 6 h at 40° C. in a drying cabinet. Before testing and further use, the film is cut into appropriately sized pieces and detached from the release liner. The single-layered wafer is stored on the release liner and is wrapped in aluminum foil.

B At first, polyvinyl alcohol (PVA) and Kollicoat® IR are dissolved in demineralized water in a beaker at a temperature of 90° C. and at a stirring speed of 400 rpm. Then, the medical substance or the medical substance solution, respectively, is added, homogenized, and the evaporation loss is compensated with demineralized water. The polymer solution is covered and left overnight and is centrifuged at 4400 rpm for 15 min on the next day in order to remove air bubbles. Then, the polymer solution is evenly spread out onto the release liner by means of a doctor blade and the polymer film is dried for 5 h at 40° C. in a drying cabinet. Before testing and further use, the film is cut into appropriately sized pieces and detached from the release liner. The single-layered wafer is stored on the release liner and is wrapped in aluminum foil.

C At first, polyvinyl alcohol (PVA) and Kollicoat® IR are dissolved in demineralized water in a beaker at a temperature of 90° C. and at a stirring speed of 400 rpm. Then, Glycerol 85% and the medical substance or the medical substance solution, respectively, are added, homogenized, and the evaporation loss is compensated with demineralized water. The polymer solution is covered and left overnight and is centrifuged at 4400 rpm for 15 min on the next day in order to remove air bubbles. Then, the polymer solution is evenly spread out onto the release liner by means of a doctor blade and the polymer film is dried for 5 h at 40° C. in a drying cabinet. Before testing and further use, the film is cut into appropriately sized pieces and detached from the release liner. The single-layered wafer is stored on the release liner and is wrapped in aluminum foil.

Example 7—Manufacture of Multi-Layered Wafers

For the manufacturing of multi-layered wafers, like those mentioned in Example 3 and Example 4, the individual layers are initially manufactured by the solvent casting method. Therefore, all ingredients of the layer are dissolved in the solvent, homogenized, and subsequently spread out to the desired thickness using a doctor blade. Then, the individual layers are either spread out one above the other or joint together in various ways such as pressure or "gluing". Thereafter, the resulting film is cut into pieces of appropriate size.

In the following, the manufacturing methods for the above-mentioned formulations of two- and three-layered wafers are described in detail:

Manufacture of Two-layered Wafers:

1. At first, the polymer solution for the mucoadhesive layer containing the active substance is manufactured according to "Manufacture of Single-layered Wafers A" and a 4% (w/v) ethyl cellulose solution EC solution in acetone is prepared. Then, the EC solution is evenly sprayed onto the release liner with the desired layer thickness and dried at room temperature for 15 min. Then, the polymer solution is evenly spread out over it by means of the doctor blade and the resulting two-layered film is dried at 40° C. for 6 h in a drying cabinet. Before testing and further use, the film is cut into appropriately sized pieces and detached from the release liner. The two-layered wafer is stored on the release liner and wrapped into aluminum foil.

2. At first, the polymer solution for the mucoadhesive, active substance containing layer is prepared according to "Manufacture of a Single-layered Wafer A" and a 4% (w/v) EC solution in acetone is prepared. The, the polymer solution is evenly spread out onto the release liner by means of a doctor blade and the polymer film is dried for 4 h at 40° C. in a drying cabinet. Then, the EC solution is evenly sprayed onto the partly dried, still sticky polymer film in the desired layer thickness. Finally, the resulting two-layered film is, again, dried for 2 h at 40° C. in a drying cabinet such that both layers firmly interconnect. Before testing and further use, the film is cut into appropriately sized pieces and pulled off the release liner. The two-layered wafer is stored on the release liner and wrapped in aluminum foil.

3. At first, the polymer solution for the mucoadhesive, active substance containing layer is prepared according to "Manufacture of a Single-layered Wafer A" and a 4% (w/v) EC solution in acetone is prepared. Then, the polymer solution is evenly spread onto the release liner by means of a doctor blade and the polymer film is dried for 4 h at 40° C. in a drying cabinet. In parallel, the EC solution is evenly sprayed onto a second release liner in the desired layer thickness and dried for 15 min at room temperature. Then, the resulting EC film is carefully detached from the release liner and is pressed onto the partly dried, still sticky polymer film by means of a roller. Finally, the now two-layered film is dried for 2 h at 40° C. in a drying cabinet such that both layers firmly interconnect. Before testing and further use, the film is cut into appropriately sized pieces and detached from the release liner. The two-layered wafer is stored on the release liner and wrapped in aluminum foil.

Manufacture of Three-Layered Wafers:

1. At first, the polymer solution for the mucoadhesive, active substance containing layer prepared according to "Manufacture of Single-layered Wafer A", a 4% (w/v) EC solution in acetone, and a 0.5% (w/v) HPMC solution in cold, demineralized water is prepared. Then, the EC solution is evenly sprayed onto the release liner with a desired layer thickness and dried for 15 min at room temperature. Then, the polymer solution is evenly spread out over it by means of a doctor blade and the resulting two-layered film is dried for 6 h at 40° C. in a drying cabinet. Finally, the HPMC solution is spread out over it as a third layer by means of a doctor blade and the resulting three-layered film is, once again, dried for 2 h at 40° C. in a drying cabinet such that all layers firmly interconnect. Before testing and further use, the film is cut into appropriately sized pieces and detached from the release liner. The three-layered wafer is stored on the release liner and wrapped into aluminum foil.

2. At first, the polymer solution for the mucoadhesive layer containing the active ingredient is prepared according to "Manufacture of Single-layered Wafers", a 4% (w/v) EC solution in acetone is prepared, and a 0.5% (w/v) HPMC solution in cold, demineralized water is prepared. Then, the EC solution is evenly sprayed onto the release liner in the desired layer thickness and dried for 15 min at room temperature. Then, the polymer solution is evenly spread out over it by means of a doctor blade and the resulting two-layered film is dried for 6 h at 40° C. in a drying cabinet. In parallel, the HPMC solution is spread out onto a second release liner with their desired layer thickness and dried for 2 h at 40° C. in a drying cabinet. Then, the HPMC film is carefully pulled off the release liner and glued onto the two-layered film with water as binder. Finally, the resulting two-layered film is dried for 1 h at 40° C. in a drying cabinet such that all layers firmly interconnect. Before testing and further use, the film is cut into appropriately sized pieces and pulled off the release liner. The three-layered wafer is stored on the release liner and wrapped into aluminum foil.

3. At first, the polymer solution for the mucoadhesive, active substance containing layer is prepared according to "Manufacture of Single-layered Wafers A", a 4% (w/v) EC solution in acetone is prepared, and a 0.5% (w/v) HPMC solution in cold, demineralized water is prepared. Then, the polymer solution is evenly spread out onto the release liner by means of a doctor blade and the polymer film is dried for 6 h at 40° C. in a drying cabinet. In parallel, the HPMC solution is spread out onto a second release liner in the desired layer thickness and dried for 1 h at 40° C. in a drying cabinet. Then, the resulting polymer film is carefully pulled off the release liner and pressed onto the partly dried, still sticky HPMC film by means of a roller. Then, the now two-layered film is dried for 1 h at 40° C. in a drying cabinet such that both layers firmly interconnect. Finally, the EC solution is evenly sprayed onto the two-layered film with a desired layer thickness and the resulting three-layered film is dried for 30 min at room temperature. Before testing and further use, the film is cut into appropriately sized pieces and pulled from the release liner. The three-layered wafer is stored on the release liner and wrapped into aluminum foil.

4. At first, the polymer solution for the mucoadhesive, active substance containing layer is prepared according to "Manufacture of Single-layered Wafers A", a 4% (w/v) EC solution in acetone is prepared, and a 0.5% (w/v) HPMC solution in cold, demineralized water is prepared. Then, the HPMC solution is spread out onto the release liner with a desired layer thickness and dried for 2 h at 40° C. in a drying cabinet. Then, the polymer solution is spread out over it by means of a doctor blade and the resulting two-layered film is dried for 4 h at 40° C. in a drying cabinet. In parallel, the EC solution is evenly sprayed onto a second release liner in the desired thickness and dried for 15 min at room temperature. Subsequently, resulting EC film is carefully pulled off the release liner and pressed onto the partly dried, still sticky two-layered film by means of a roller. Finally, the now three-layered film is dried for 2 h at 40° C. in a drying cabinet such that all layers firmly interconnect. Before testing and further use, the film is cut into appropriately sized pieces and pulled off the release liner. The three-layered wafer is stored on the release liner and wrapped into aluminum foil.

The features of the present invention disclosed in the description above, in the claims, and in the drawings can be essential both individually and also in any combination for implementing the invention in its various embodiments.

Figure 9A:
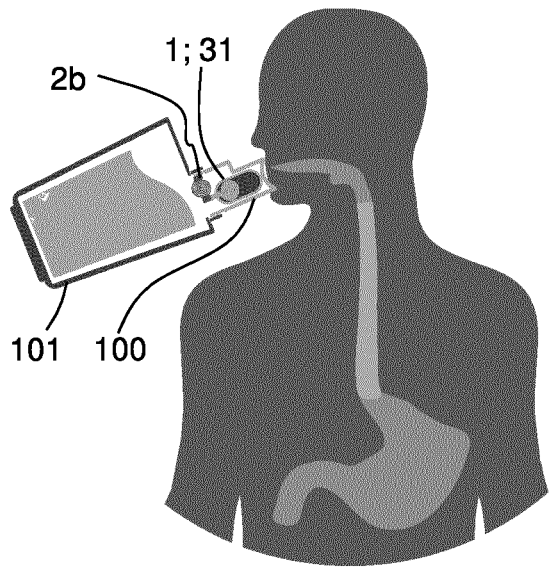
FIG. 9a shows an illustration explaining a first step of a procedure including the administration of a swallowable dosage form being configured according to the invention.
Figure 9B:
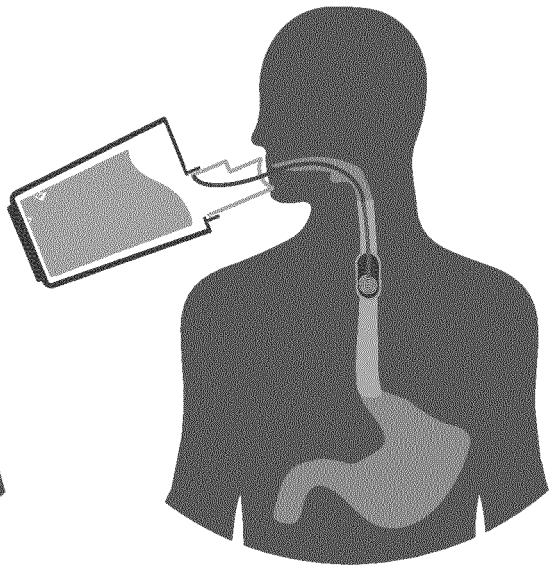
Figure 9C:
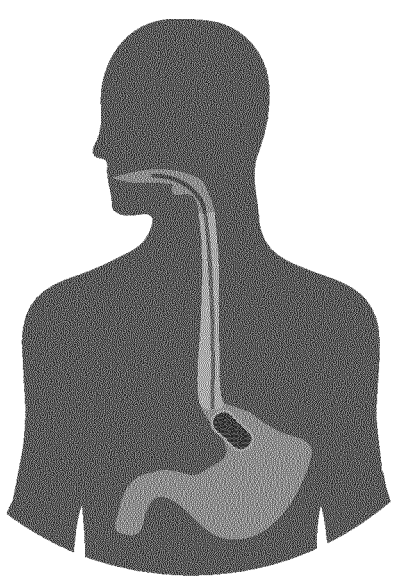
Figure 9D:
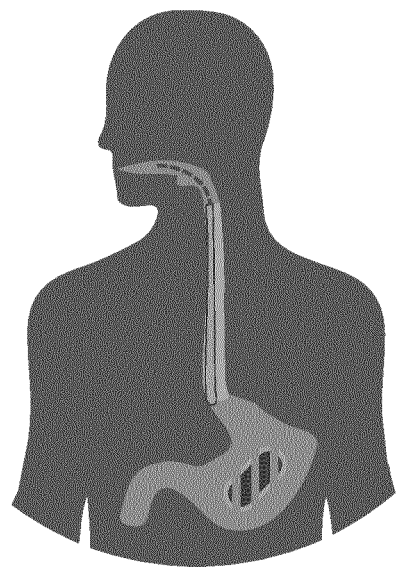

Especially, the exemplary embodiments of the invention relate to an orally administrable dosage form for the treatment of the esophageal mucosa. An exemplary process of administering the dosage form by swallowing the same is shown in FIGS. 9a to 9d. An applicator 100 is used, which contains a pharmaceutical dosage from according to the invention. A coiled string member 2b is connected to the end portion 2a of the preparation 2 of the dosage form (1 or 31). The applicator is connected to a vessel 101 with water. Drinking from the applicator involves rinsing of the applicator by the water inside the vessel and thereby transporting the dosage form into the mouth of the patient, while the string member 2b stays connected to the applicator. After the dosage form is fully swallowed and arrived in the stomach of the patient (FIG. 9c) the patient removes the end portion of the string member 2b and connects the same to the teeth for fixating the string member and the preparation in its expanded condition, where it is located inside the esophagus. In this case, the preparation 2 can deliver useful substances such as an active pharmaceutical ingredient to the esophageal mucous membrane by unrolling its sheet like preparation 2 while moving along the esophagus when it is swallowed (FIG. 9b, c). Thus, active pharmaceutical ingredients contained in the sheet like preparation 2 can be locally released to the mucous membrane of the esophagus. Current treatments for local diseases of the esophagus generally employ swallowing the content of application systems, which were designed for inhalation therapy of the lung, or swallowing a gel containing specific drugs. However, generally the swallowed content of the application systems or the gel only has a short contact time with the esophageal mucosa. Therefore, the local effect is decreased and the systemic effect is increased, in particular, compared to an application form, in which the contact time is prolonged. By applying the sheet like preparation 2 to the esophageal mucosa a pharmaceutical dosage form according to the embodiment of the invention the treatment of local diseases of the esophagus can be improved and, in particular, the contact time can be prolonged and the reliability of the process of pulling out the preparation from the capsule and, thus, the reliability of the overall administration process is improved. When applied to the esophageal mucosa, the sheet like preparation 2 stays in contact with the mucosa whilst providing a controlled release of the active pharmaceutical ingredient in order to achieve a local therapy or diagnosis. Preferably, the controlled release can neither be immediate, sustained or prolonged, also preferably, during or after the release of the active pharmaceutical ingredient or the active pharmaceutical ingredients the sheet like preparation 2 dissolves and is, preferably swallowed. Moreover, the shell (=capsule) 3 may detach from the sheet like preparation 2 immediately after the release of the sheet like preparation 2 (FIG. 9c, d) or may dissolve while still attached to the sheet like preparation 2. Preferably, the shell 3 is made of a dissolvable and/or digestible material. In particular, the end portion 2a may be adapted to be fixed in the oral cavity. Therefore, the end portion 2 may include a mucoadhesive surface, preferably comprising cellulose derivates, starch and starch derivates, polyvinyl alcohol, polyethylene oxide, polyethylene, polypropylene, polyacrylic acid and polyacrylate derivates, polyvinylpyrollidone, Povidone, Copovidone, sodium alginate, gelatin, xanthan gum, guar gum, Carrageenan, pectins, dextrans, lectins, Chitosan, Pullulan an mixtures thereof. So, preferably, the holding device 5 can be attached to the oral mucosa, in particular the buccal mucosa, i.e. the inside of the cheek.

Even more specifically, the embodiments of the invention may refer to a pharmaceutical dosage form for the treatment of eosinophilic esophagitis. Eosinophilic esophagitis is an inflammatory, immune-mediated disease with increasing relevance in gastrointestinal disorders. This disease can be treated with topic steroids. Preferably, the shell 3 is a capsule made out of hard gelatin. In an initial state of the dosage form, the sheet like preparation 2 is in a compact form, in particular in form of a coil, and is connected to an applicator containing the dosage form and water at an initial phase. On administration, the end portion 2a is attached in the oral cavity, preferably to the buccal mucosa, in particular by gluing it to the mucosa. Next, the dosage form is swallowed, preferably with a beverage or water, and, therefore, the dosage form moves along the esophagus and a force acts on the end portion 2a by conveying the capsule towards the stomach. While the dosage form moves down the esophagus the sheet like preparation 1 is unrolled, and thus released. Preferably, the sheet like preparation is mucoadhesive, and thus may adhere to the mucous membrane of the esophagus. In this case, the contact and/or position of the sheet like preparation is not or is not only dependent on the positin o the end portion 2a in the oral cavity. Afterwards, an oblong region of the esophageal mucosa is covered or at least near to the sheet like preparation 2. Thus, it can be treated with active pharmaceutical ingredients, in particular topic steroids, released by the sheet like preparation 2. Preferably, the sheet like preparation 2 may comprise and release fluticasone or budesonide.

Preferably, the manufacture of a sheet like preparation 2, in particular according to the embodiments of the present invention, is carried out by a solvent casting method, wherein at first all ingredients are dissolved in the solvent, homogenized, and subsequently spread out on a suitable release liner to the desired thickness using a doctor blade. Then, the resulting film is dried under defined conditions and then cut into pieces of suitable size.

In a preferred variant, the ingredients, particularly the polymer matrix, consists of 10% m/m polyvinyl alcohol (PVA) (Mowiol 40-88) suspended in a 20% m/m Kollicoat IR aqueous solution. Furthermore, the active pharmaceutical ingredient such as fluticasone or budesonide as well as additives such as methylene blue as a visual control is added.

A sheet like preparation 2 manufactured according to this preferred variant has been experimentally analyzed. For this purpose the sheet like preparation 2 was tested for film thickness and uniformity of mass. Furthermore, disintegration time was tested both and purified water and on wetted are alginate gel (3% m/m) to simulate the mucosa. Fully disintegration was defined as the absence of any solid matrix particle. Tensile strength, elongation and extraction force have been measured using a texture analyzer. All tests were performed triplicate and mean plus/minus standard derivation are reported. The resulting sheet like preparation 3 had a thickness of 114±5 μm and a mean mass of 9.39±0.03 mg/cm$^2$. The disintegration time in water was 760±35 s, and greater than 1200 s on alginate gel. The tensile strength was 31.35 MPa. The elongation at break was 7.41±0.90%.

Preferably, a pharmaceutical dosage form, in particular according to the embodiments of the present invention, may be manufactured as described in the following:
cutting the film resulting from a solvent casting technique to strips of 400 mm by 4 mm;
folding or rolling the resultant sheet like preparations 2;
providing a hard gelatin capsule of size 1 is a shell 3;
milling an opening 5 into a part of the hard gelatin capsule 3, specifically, as illustrated, into the upper part;
threading one end of the sheet like preparation 2 through the opening 5; and
closing the capsule.

A dosage form manufactured as described above comprising the preferred variant of the sheet like preparation 2, in particular for the embodiments of the present invention, has been experimentally analyzed, as described above. The extraction force of the sheet like preparation 2 from the capsule was documented in diagram of FIG. 8.

Furthermore, as shown in FIG. 4f, the sheet like preparation 2 may optionally comprise two regions, a first region of the sheet like preparation 2c and a second region of the sheet like preparation 2c. The first region 2c is pulled out from the opening, and the second region 2c is pulled out following the first region 2c. The first region 2c and the second region 2d may comprise different active pharmaceutical ingredients. Preferably, the first region 2c can comprise local anesthetics such as benzocaine, butamben, dibucaine, lidocaine, oxybuprocaine or novocaine, and the second region 2d can comprise a steroid such as corticosteroids, glucocorticoids, fluticasone, budesonide or clocortolone. In particular, in this way, when treating the esophagus, a gag reflex can be suppressed by the local anesthetic and the esophageal mucous membrane can be treated with the steroid. Additionally, the first region 2c has a smaller cross-sectional area than the second region 2d. In particular, this beneficially facilitates swallowing the dosage form.

Furthermore, the end portion 2a is connected to the sheet like preparation 2 or is a broadened part of the sheet like preparation 2 with a mucoadhesive layer preferably comprising: mucoadhesive polymers such as cellulose derivatives, starch and starch derivatives, sodium alginate, gelatin, xanthan gum, guar gum, carrageenan, pectins, dextrans, lectins, and mixtures thereof.

Preferably, the preparation 2 is manufactured according to one manufacturing method described in here. In particular, the sheet like preparation with multiple regions, especially at least a first region 2c and at least a second region 2d, can be manufactured similarly to a multi-layered preparation, wherein, at least some of, the layers are offset to each other but still partially overlap. Also the end portion 2a may be manufactured and/or connected to the sheet like preparation 2 in this way.

I claim:

1. A pharmaceutical dosage form for the application to a mucous membrane, comprising
    at least one preparation having an elongated shape and comprising an active pharmaceutical ingredient, wherein the preparation has a string-like, strip-like or sheet-like shape or is film-shaped, foil-shaped or wafer-shaped, and wherein the at least one preparation is capable of being arranged in a compact condition or in an expanded condition, and
    a capsule device comprising a hollow space for accommodating the at least one preparation being in the compact condition, the capsule device having an opening and a first end of the preparation extending, in the compact condition, through the opening for allowing pulling out the preparation from the hollow space into the surrounding area of the capsule device thereby transferring the preparation from the compact condition to the expanded condition,
        wherein the opening and the preparation being dimensioned such that, when the preparation is pulled out from the opening, a spacing is provided in an opening cross section of the opening between the preparation and a surface of the capsule device defining the opening,
        wherein the capsule device extends along a central length axis of the capsule device,
        wherein the opening is arranged such that a central point of the opening is offset from the central length axis,
        and wherein the opening is a slit-like opening configured for allowing a strip-like preparation to pass through the opening, the cross section of the opening being larger than the cross section of the strip-like preparation, when the latter is moving through the opening.

2. A pharmaceutical dosage form according to claim 1, wherein the slit-like opening has two opposing edges, which extend along a main plane of the slit-like opening, the main plane being defined by a first line and a second line, the first line being perpendicular to the central length axis of the capsule device, the second line being perpendicular to the first line and including an angle $\alpha$ with the central length axis, and the normal of the main plane including an angle $\alpha$ with the central length axis, wherein $0 <= \alpha <= 90°$.

3. A pharmaceutical dosage form according to claim 2, wherein $1° < \alpha <= 90°$.

4. A pharmaceutical dosage form according to claim 2, wherein $\alpha = 45°$.

5. A pharmaceutical dosage form according to claim 2, wherein $\alpha = 90°$.

6. A pharmaceutical dosage form according to claim 1, wherein a width of the slit-like opening is larger than a thickness of the strip-like preparation, which is moved out of the capsule device through the slit-like opening.

7. A pharmaceutical dosage form according to claim 1, wherein the spacing is from 100 µm to 2000 µm.

8. A pharmaceutical dosage form according to claim 1, wherein the capsule device comprises at least one guiding member, which is arranged inside the inner space of the capsule device to guide the motion of the string-like or sheet like preparation towards the opening of the capsule device.

9. A pharmaceutical dosage form according to claim 8, wherein the at least one guiding member forms a guiding compartment for accommodating and guiding the preparation.

10. A pharmaceutical dosage form according to claim 1, wherein the capsule device is configured to be suitable to be swallowed by a patient.

11. A pharmaceutical dosage form according to claim 1, wherein the capsule device comprises a first tube element, and further comprises an additional second tube element, wherein the second tube element has at least partially a smaller tube diameter than the first tube element, and wherein the second tube element is arranged at least partially in the first tube element and is thereby connected to the first tube element.

12. A pharmaceutical dosage form according to claim 1, wherein the capsule device comprises a first half-cylinder element, and the capsule device further comprises a second half-cylinder element, which is connected to the first half-cylinder element to form the capsule device.

13. A pharmaceutical dosage form according to claim 1, wherein the pharmaceutical dosage form comprises a sinker device, which occupies a part of the hollow space and which provides an additional weight to the pharmaceutical dosage form.

14. A method for producing a capsule device for a pharmaceutical dosage form according to claim 1, comprising the steps of:
    providing a material for forming a capsule device;
    generating an opening or a slit-like opening, in the material of the capsule device; and
    forming the capsule device.

15. A method for producing the pharmaceutical dosage form according to claim 1, comprising the steps of:
    providing a capsule device having an opening;
    compacting the active pharmaceutical ingredient;
    shaping the active pharmaceutical ingredient, during the compacting step, into an elongated preparation having two end portions;
    placing the elongated, compacted preparation, inside the hollow space of the capsule device;
    extending an end portion of the preparation through the opening, wherein the opening and the preparation are configured such that when the preparation is pulled out from the opening, a spacing is provided in the opening cross section of the opening between the preparation and a surface of the capsule device defining the opening.

16. The pharmaceutical dosage form for the application to a mucous membrane according to claim 1, wherein said membrane is selected from the group consisting of buccal, gastro-intestinal, rectal, vaginal membranes and combinations thereof.

17. The pharmaceutical dosage form for the application to a mucous membrane according to claim 16, wherein said membrane is a gastro-intestinal membrane.

18. The pharmaceutical dosage form for the application to a mucous membrane according to claim 16, wherein said membrane is an esophageal membrane.

19. The pharmaceutical dosage form according to claim 1, comprising the active pharmaceutical ingredient selected from the group consisting of insulin, buserelin, desmospression, calcintonin, estrogen, and the antibody rituximab.

20. The pharmaceutical dosage form according to claim 13, wherein the sinker device is configured to provide a negative buoyancy to the pharmaceutical dosage form.

* * * * *